United States Patent
Iyoku et al.

(10) Patent No.: US 10,765,619 B2
(45) Date of Patent: Sep. 8, 2020

(54) SILICONE RESIN, MAKING METHOD, AND COSMETICS

(71) Applicant: SHIN-ETSU CHEMICAL CO., LTD., Tokyo (JP)

(72) Inventors: Hiroomi Iyoku, Akron, OH (US); Yuji Ando, Annaka (JP)

(73) Assignee: SHIN-ETSU CHEMICAL CO., LTD., Tokyo (JP)

(*) Notice: Subject to any disclaimer, the term of this patent is extended or adjusted under 35 U.S.C. 154(b) by 31 days.

(21) Appl. No.: 15/997,053

(22) Filed: Jun. 4, 2018

(65) Prior Publication Data

US 2019/0365632 A1    Dec. 5, 2019

(51) Int. Cl.

| A61K 8/891 | (2006.01) |
|---|---|
| A61Q 1/02 | (2006.01) |
| A61Q 1/06 | (2006.01) |
| A61Q 1/08 | (2006.01) |
| A61Q 1/10 | (2006.01) |
| A61Q 17/04 | (2006.01) |
| A61Q 3/02 | (2006.01) |
| A61Q 19/00 | (2006.01) |
| A61Q 15/00 | (2006.01) |
| A61Q 19/10 | (2006.01) |
| A61Q 5/12 | (2006.01) |
| A61Q 5/00 | (2006.01) |
| C08G 77/02 | (2006.01) |

(52) U.S. Cl.
CPC .......... *A61K 8/891* (2013.01); *A61Q 1/02* (2013.01); *A61Q 1/06* (2013.01); *A61Q 1/08* (2013.01); *A61Q 1/10* (2013.01); *A61Q 3/02* (2013.01); *A61Q 5/00* (2013.01); *A61Q 5/12* (2013.01); *A61Q 15/00* (2013.01); *A61Q 17/04* (2013.01); *A61Q 19/00* (2013.01); *A61Q 19/007* (2013.01); *A61Q 19/10* (2013.01); *C08G 77/02* (2013.01)

(58) Field of Classification Search
CPC .......... C07F 7/18; C07F 7/0836; C08G 77/045
See application file for complete search history.

(56) References Cited

U.S. PATENT DOCUMENTS

| 7,989,002 B2 | 8/2011 | Shah et al. |
|---|---|---|
| 8,883,128 B2 | 11/2014 | Bui et al. |
| 2011/0052815 A1* | 3/2011 | Fritsche .......... C03C 17/25 427/282 |

FOREIGN PATENT DOCUMENTS

| JP | 62-234012 A | 10/1987 |
|---|---|---|
| JP | 62-298511 A | 12/1987 |
| JP | 4-59284 B2 | 9/1992 |
| JP | 6-15448 B2 | 3/1994 |
| JP | 2009-19033 A | 1/2009 |
| JP | 5512278 B2 | 6/2014 |
| JP | 2016-117701 A | 6/2016 |
| JP | 2018-2643 A | 1/2018 |

* cited by examiner

*Primary Examiner* — Kuo Liang Peng
(74) *Attorney, Agent, or Firm* — Birch, Stewart, Kolasch & Birch, LLP

(57) ABSTRACT

A silicone resin represented by formula (1) and having a Mw of 1,000-8,000 is useful in cosmetics.

$$[(C_6H_5)_3SiO_{1/2}]_a[R^1{}_3SiO_{1/2}]_b[R^2{}_2SiO_{2/2}]_c[R^3SiO_{3/2}]_d [SiO_{4/2}]_e \quad (1)$$

$R^1$ is a $C_1$-$C_8$ alkyl group, $C_6$-$C_{12}$ aryl group (exclusive of phenyl) or $C_1$-$C_8$ fluorinated alkyl group, $R^2$ and $R^3$ are each independently a $C_1$-$C_8$ alkyl group, $C_6$-$C_{12}$ aryl group or $C_1$-$C_8$ fluorinated alkyl group, a=0-0.2, b=0.1-0.5, c=0-0.2, d=0.01-0.5, e=0-0.6, a+b+c+d+e=1.0, at least one phenyl group is included in the molecule. A film of the silicone resin has a refractive index of at least 1.48.

6 Claims, No Drawings

SILICONE RESIN, MAKING METHOD, AND COSMETICS

TECHNICAL FIELD

This invention relates to a silicone resin having phenyl group (sometimes referred to as phenylsilicone resin, hereinafter), a method for preparing the same, and a cosmetic composition comprising the same.

BACKGROUND ART

In the prior art, silicone resins are widely used as cosmetic ingredients in make-up cosmetics (e.g., foundations, lipsticks, eye shadows and mascaras), UV care cosmetics, and hair care cosmetics because of their film-forming ability, water resistance, sweat resistance and sebum resistance. For example, Patent Document 1 discloses a skin care cosmetic composition comprising an organic silicone resin comprising units having the average formula: $R_nSiO_{(4-n)/2}$ and a volatile hydrocarbon oil. Patent Document 2 discloses a skin care cosmetic composition comprising a resin comprising $R_3SiO_{1/2}$ units and $SiO_{4/2}$ units and a volatile silicone oil. Patent Document 3 discloses a sunscreen cosmetic composition comprising a silicone resin comprising at least two of $R_2SiO_{2/2}$ units, $RSiO_{3/2}$ units and $SiO_{4/2}$ units, optionally end-capped with a $R_3SiO_{1/2}$ unit, a volatile oil, and a UV absorbing agent and/or UV scattering agent. Patent Document 4 discloses a skin care cosmetic composition comprising 1 to 70% by weight of an organic silicone resin comprising at least 70 mol % of $R_3SiO_{1/2}$ units and $SiO_{4/2}$ units, with a molar ratio of $R_3SiO_{1/2}$ units to $SiO_{4/2}$ units ranging from 0.5/1 to 1.5/1. Allegedly these compositions form films having water resistance.

Nowadays, further improvements in water resistance, sweat resistance and long lasting performance are demanded as well as luster and color development. Phenylsilicone resins having a high phenyl content are developed to meet such demands. However, the phenylsilicone resins having a high phenyl content are less compatible with silicone and organic oily ingredients. In Patent Documents 5 to 7, they are formulated with a UV absorber or an oil such as a liquid oil having a high polarity as demonstrated by an inorganic value/organic value (JOB) of at least 0.2. This suggests that cosmetic formulations containing a phenylsilicone resin having a high phenyl content are limitative. Patent Document 8 discloses a cosmetic composition comprising a silicone resin comprising $R^1_3SiO_{1/2}$ units, $R^2_2SiO_{2/2}$ units, $R^3SiO_{3/2}$ units, and $SiO_{4/2}$ units, but refers nowhere to the refractive index of a film.

CITATION LIST

Patent Document 1: JP-B H04-59284
Patent Document 2: JP-B H06-15448
Patent Document 3: JP-A S62-234012
Patent Document 4: JP-A S62-298511
Patent Document 5: JP-A 2016-117701
Patent Document 6: JP-A 2009-019033 (U.S. Pat. No. 8,883,128)
Patent Document 7: JP 5512278 (U.S. Pat. No. 7,989,002)
Patent Document 8: JP-A 2018-002643

SUMMARY OF INVENTION

An object of the invention is to provide a phenylsilicone resin which is soluble in organic oily ingredients such as silicone oils and hydrocarbon oils, able to form a uniform continuous film free of stickiness and brittleness, and compatible with UV absorbers, and a method for preparing the same. Another object is to provide a cosmetic composition comprising the phenylsilicone resin, which offers a pleasant feel on use (e.g., ease to spread on application, no sticky feeling, no color irregularity on finishing, and long lasting), and eliminates secondary staining or transfer to clothes or the like.

The inventors have found that a phenylsilicone resin comprising specific constituent units is soluble in oily ingredients such as silicone oils and organic oils, able to form a uniform continuous film free of sticky feel and brittleness, and compatible with UV absorbers, and that a cosmetic composition comprising the phenylsilicone resin offers a pleasant feel on use and eliminates secondary staining or transfer to clothes or the like.

The invention is as follows.

1. A silicone resin represented by the compositional formula (1) and having a weight average molecular weight of 1,000 to 8,000,

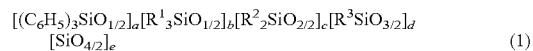

wherein $R^1$ is a group, exclusive of phenyl, selected from among $C_1$-$C_8$ alkyl groups, $C_6$-$C_{12}$ aryl groups and $C_1$-$C_8$ fluorinated alkyl groups, $R^2$ and $R^3$ are each independently a group selected from among $C_1$-$C_8$ alkyl groups, $C_6$-$C_{12}$ aryl groups and $C_1$-$C_8$ fluorinated alkyl groups, a is a number of 0 to 0.2, b is a number of 0.1 to 0.5, c is a number of 0 to 0.2, d is a number of 0.01 to 0.5, e is a number of 0 to 0.6, a+b+c+d+e is equal to 1.0, $R^1$ to $R^3$ and a to e are selected such that at least one phenyl group is included in the molecule, a film of the silicone resin having a refractive index of at least 1.48.

2. The silicone resin of 1, having a phenyl content of at least 30% by weight.

3. The silicone resin of 1 or 2 wherein in formula (1), a is a number of 0.01 to 0.2.

4. The silicone resin of any one of 1 to 3 wherein in formula (1), $R^3$ is phenyl.

5. The silicone resin of any one of 1 to 4 wherein in formula (1), c is 0, $R^1$ is methyl, and $R^3$ is phenyl.

6. The silicone resin of any one of 1 to 5 which is soluble in at least one selected from the group consisting of decamethylcyclopentasiloxane, isododecane or octyl p-methoxycinnamate in a silicone resin concentration of 50% by weight.

7. A method for preparing the silicone resin of 3, comprising the steps of:

(i) effecting hydrolytic condensation of at least one organosilicon compound selected from the general formulae (2) and (3):

wherein $R^1$ is as defined above with at least one compound selected from silanes having the general formulae (4), (5) and (6):

wherein $R^2$ and $R^3$ are as defined above, $R^4$ is each independently hydrogen or a substituted or unsubstituted monovalent hydrocarbon group and partial hydrolytic condensates thereof, in a solventless system or a solvent, and (ii) adding triphenylsilanol and a solvent to the hydrolytic condensate, and effecting condensation of the hydrolytic condensate with triphenylsilanol in the presence of a weakly basic catalyst.

8. The method of 7 wherein the weakly basic catalyst is sodium hydrogencarbonate or sodium acetate.

9. A cosmetic composition comprising 0.1 to 40% by weight of the silicone resin of any one of 1 to 6.

10. The cosmetic composition of 9, further comprising an oil selected from silicone oils, hydrocarbon oils, ester oils, and glyceride oils.

11. The cosmetic composition of 9 or 10, further comprising a surfactant.

12. The cosmetic composition of 11 wherein the surfactant is at least one surfactant selected from among linear or branched organopolysiloxanes having a polyoxyalkylene or polyglycerol group and alkyl-co-modified organopolysiloxanes thereof.

13. The cosmetic composition of any one of 9 to 12, further comprising an admixture of a crosslinked organopolysiloxane polymer and a liquid oil.

14. The cosmetic composition of 13 wherein the crosslinked organopolysiloxane polymer is a crosslinked organopolysiloxane polymer having a polyether or polyglycerol group.

15. The cosmetic composition of any one of 9 to 14, further comprising a film-forming agent selected from among silicone resins, exclusive of the silicone resin defined above, comprising constituent units: $[R^5_3SiO_{1/2}]$, $[R^6_2SiO_{2/2}]$, $[R^7SiO_{3/2}]$, and $[SiO_{4/2}]$ wherein $R^5$, $R^6$ and $R^7$ are each independently a group selected from among $C_1$-$C_8$ alkyl groups, $C_6$-$C_{12}$ aryl groups and $C_1$-$C_8$ fluorinated alkyl groups, and linear acrylic-silicone copolymers.

16. The cosmetic composition of any one of 9 to 15, further comprising a powder.

17. The cosmetic composition of any one of 9 to 16, further comprising a UV absorbing agent or UV absorbing/scattering agent.

18. The cosmetic composition of any one of 9 to 17, which is a skin care cosmetic, hair care cosmetic, make-up cosmetic, UV care cosmetic or antiperspirant.

Advantageous Effects of Invention

The phenylsilicone resin of the invention is soluble in oily ingredients such as silicone oils and organic oils, able to form a uniform continuous film free of sticky feel and brittleness, and compatible with UV absorbers. The cosmetic composition comprising the phenylsilicone resin offers a pleasant feel on use and eliminates secondary transfer.

DESCRIPTION OF PREFERRED EMBODIMENTS

The notation (Cn-Cm) means a group containing from n to m carbon atoms per group.

The invention includes embodiment I relating to a phenylsilicone resin, embodiment II relating to a method for preparing the phenylsilicone resin, and embodiment III relating to a cosmetic composition comprising the phenylsilicone resin, which are described below in order.

I. Phenylsilicone Resin

Embodiment I of the invention is a silicone resin represented by the compositional formula (1).

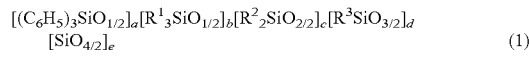

$$[(C_6H_5)_3SiO_{1/2}]_a[R^1_3SiO_{1/2}]_b[R^2_2SiO_{2/2}]_c[R^3SiO_{3/2}]_d[SiO_{4/2}]_e \quad (1)$$

Herein $R^1$ is a group, exclusive of phenyl, selected from among $C_1$-$C_8$ alkyl groups, $C_6$-$C_{12}$ aryl groups and $C_1$-$C_8$ fluorinated alkyl groups, $R^2$ and $R^3$ are each independently a group selected from among $C_1$-$C_8$ alkyl groups, $C_6$-$C_{12}$ aryl groups and $C_1$-$C_8$ fluorinated alkyl groups, a is a number of 0 to 0.2, b is a number of 0.1 to 0.5, c is a number of 0 to 0.2, d is a number of 0.01 to 0.5, e is a number of 0 to 0.6, a+b+c+d+e is equal to 1.0. $R^1$ to $R^3$ and a to e are selected such that at least one phenyl group is included in the molecule.

Suitable $C_1$-$C_8$ alkyl groups include methyl, ethyl, propyl, butyl, pentyl, hexyl, heptyl and octyl. Suitable $C_6$-$C_{12}$ aryl groups include phenyl and tolyl. Typical of the $C_1$-$C_8$ fluorinated alkyl group is trifluoropropyl. $R^1$, $R^2$ and $R^3$ may be different in the molecule.

Specifically, $R^1$ is preferably $C_1$-$C_3$ alkyl, with methyl being more preferred. $R^2$ is preferably $C_1$-$C_3$ alkyl, with methyl being more preferred. $R^3$ is preferably $C_1$-$C_3$ alkyl or phenyl, with methyl and phenyl being more preferred.

The subscript "a" is a number of 0 to 0.2, preferably 0.01 to 0.2, more preferably 0.03 to 0.1. If a is more than 0.2, then triphenylsilanol may become less reactive, suggesting the risk that triphenylsilanol is left during resin preparation and the resulting resin contains impurities. The subscript b is a positive number of 0.1 to 0.5, preferably 0.2 to 0.45, more preferably 0.2 to 0.4. If b is less than 0.1, the film becomes hard and brittle. If b is more than 0.5, the film becomes sticky. The subscript c is a number of 0 to 0.2, preferably 0 to 0.15. If c is more than 0.2, the film becomes hard and brittle. The subscript d is a number of 0.01 to 0.5, preferably 0.05 to 0.45, more preferably 0.1 to 0.4. If d is less than 0.01, the film becomes sticky, and there is a risk that when triphenylsilanol is used for resin preparation, triphenylsilanol is left behind and the resulting resin contains impurities. If d is more than 0.5, the film becomes hard and brittle. The subscript e is a number of 0 to 0.6. If d is more than 0.6, the film becomes hard and brittle. The sum a+b+c+d+e is equal to 1.0.

The silicone resin of compositional formula (1) wherein c is 0, $R^1$ is methyl, and $R^3$ is phenyl is preferred. That is, a silicone resin represented by the following compositional formula (1-2) is preferred.

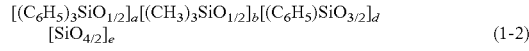

$$[(C_6H_5)_3SiO_{1/2}]_a[(CH_3)_3SiO_{1/2}]_b[(C_6H_5)SiO_{3/2}]_d[SiO_{4/2}]_e \quad (1-2)$$

Herein a is a number of 0 to 0.2, b is a number of 0.1 to 0.5, d is a number of 0.01 to 0.5, e is a number of 0 to 0.6, and a+b+d+e is equal to 1.0.

The phenylsilicone resin should have a weight average molecular weight (Mw) of 1,000 to 8,000, preferably 2,000 to 7,000, more preferably 2,000 to 6,000. If Mw is too low, the resin becomes a high viscosity liquid, failing to form a film. If Mw is too high, the resin becomes less soluble in solvents. It is noted that Mw is measured versus polystyrene standards by gel permeation chromatography (GPC) using tetrahydrofuran (THF) solvent. A suitable chromatograph is available from Tosoh Corp., for example.

A film formed of the phenylsilicone resin should have a refractive index of at least 1.48, preferably 1.490 to 1.520. It is noted that refractive index is measured by removing solvent from a phenylsilicone resin solution to form a film having a thickness of about 1 mm, and analyzing the film at a temperature of 25° C. by means of a refractometer, for example, Abbemat (Anton Paar GmbH).

Since a film having the desired refractive index is obtainable by adjusting the phenyl content of the silicone resin, the silicone resin should preferably have a phenyl content of at least 30% by weight, more preferably 31 to 40% by weight.

When a phenylsilicone resin having a specific phenyl content and refractive index is formulated in a cosmetic composition, the cosmetic composition offers a pleasant feel on use, typically ease of spreading on application, non-sticky feeling, and lasting performance due to water resistance and tight skin adhesion, and prevents secondary staining or transfer to clothes or the like.

Since the phenylsilicone resin is solid at normal temperature, it may take the form of solid by grinding or solution by diluting with an oil which is permitted for use in cosmetics. Suitable oils are organic oily ingredients including silicone oils and hydrocarbon oils, typically decamethylcyclopentasiloxane, isododecane and octyl p-methoxycinnamate. Preferably the phenylsilicone resin is soluble in at least one oil selected from the group consisting of decamethylcyclopentasiloxane, isododecane and octyl p-methoxycinnamate in a silicone resin concentration of 50% by weight. Notably, the solubility of the phenylsilicone resin may be adjusted by a balance of Mw and refractive index of the resin.

II. Preparation of Phenylsilicone Resin

Embodiment II of the invention is a method for preparing the silicone resin, comprising the following steps. In one embodiment (A) wherein a is equal to 0, the method comprises the steps of:

(A-i) effecting hydrolytic condensation of at least one organosilicon compound selected from the general formulae (2) and (3):

$$R^1{}_3SiOSiR^1{}_3 \quad (2)$$

$$R^1{}_3SiOH \quad (3)$$

wherein $R^1$ is as defined above with at least one compound selected from silanes having the general formulae (4), (5) and (6):

$$(R^4O)_2SiR^2{}_2 \quad (4)$$

$$(R^4O)_3SiR^3 \quad (5)$$

$$(R^4O)_4Si \quad (6)$$

wherein $R^2$ and $R^3$ are as defined above, $R^4$ is each independently hydrogen or a substituted or unsubstituted monovalent hydrocarbon group, with the proviso that at least one of $R^2$ and $R^3$ is phenyl, and partial hydrolytic condensates thereof, the compound essentially containing a silane of formula (5), in a solventless system or a solvent, and (A-ii) adding a solvent to the hydrolytic condensate, and effecting condensation of the hydrolytic condensate in the presence of a weakly basic catalyst.

In another embodiment (B) wherein a is not equal to 0, the method comprises the steps of:

(B-i) effecting hydrolytic condensation of at least one organosilicon compound selected from the general formulae (2) and (3):

$$R^1{}_3SiOSiR^1{}_3 \quad (2)$$

$$R^1{}_3SiOH \quad (3)$$

wherein $R^1$ is as defined above with at least one compound selected from silanes having the general formulae (4), (5) and (6):

$$(R^4O)_2SiR^2{}_2 \quad (4)$$

$$(R^4O)_3SiR^3 \quad (5)$$

$$(R^4O)_4Si \quad (6)$$

wherein $R^2$ and $R^3$ are as defined above, $R^4$ is each independently hydrogen or a substituted or unsubstituted monovalent hydrocarbon group and partial hydrolytic condensates thereof, the compound essentially containing a silane of formula (5), in a solventless system or a solvent, and (B-ii) adding triphenylsilanol and a solvent to the hydrolytic condensate, and effecting condensation of the hydrolytic condensate with triphenylsilanol in the presence of a weakly basic catalyst.

Herein, $R^1$, $R^2$ and $R^3$ are as defined above, and $R^4$ is each independently hydrogen or a substituted or unsubstituted monovalent hydrocarbon group, preferably $C_1$-$C_4$ alkyl. It is noted that in embodiment (A), at least one of $R^2$ and $R^3$ is phenyl. The compounds having formulae (2) to (6) may be used alone or in any desired combination of two or more. $R^1$, $R^2$, $R^3$, and $R^4$ may be different in the molecule.

Step (i): (A-i) and (B-i)

Step (i) is hydrolytic condensation of an organosilicon compound with a silane or partial hydrolytic condensate thereof in a solventless system or a solvent.

The hydrolytic condensation is conducted preferably under acidic conditions and more preferably an acidic substance is added as the catalyst. Suitable acidic substances include hydrochloric acid, sulfuric acid, p-toluenesulfonic acid, methanesulfonic acid, trifluoromethanesulfonic acid, phosphoric acid, acetic acid and citric acid while they may be used alone or in admixture. The acidic substance may be added in a small amount, preferably in an amount of 0.001 to 10% by weight of the entire hydrolytic condensation reaction system.

The hydrolytic condensation may be conducted in a solventless system or a solvent, preferably in a solvent. Examples of the solvent used in step (i) include hydrocarbon solvents such as toluene, xylene and isoparaffin, ether solvents such as tetrahydrofuran, and aliphatic alcohols of 1 to 10 carbon atoms such as methanol, ethanol, (iso)propyl alcohol, and butanol, which may be used alone or in admixture. Inter alia, aliphatic alcohols of 1 to 10 carbon atoms are preferred, with ethanol and isopropyl alcohol (IPA) being more preferred. The solvent is preferably used in an amount of 5 to 50% by weight of the entire hydrolytic condensation reaction system.

Specifically, a reactor is charged with the organosilicon compound, the silane or partial hydrolytic condensate thereof, and a solvent, and an acid is added. With stirring, water is added dropwise. During dropwise addition of water, the reactor is kept at a temperature of 0 to 60° C., preferably 0 to 40° C. The amount of water added is preferably such that a molar ratio of water to hydrolyzable group may range from 0.6/1 to 2.5/1. After the dropwise addition of water, hydrolytic condensation reaction is continued preferably while heating at 30 to 100° C., especially 50 to 80° C. for 2 to 8 hours.

The hydrolysis is followed by acid removal. The acid may be removed by neutralizing with an alkali metal carbonate, alkali metal hydrogencarbonate or alkali metal hydroxide, or by washing with water.

Step (ii): (A-ii) and (B ii)

Step (ii) is to add a solvent to the hydrolytic condensate and to effect condensation of the hydrolytic condensate with triphenylsilanol in the presence of a weakly basic catalyst.

In embodiment (B-ii), step (ii) is to add triphenylsilanol and a solvent to the hydrolytic condensate and to effect condensation of the hydrolytic condensate with triphenylsilanol in the presence of a weakly basic catalyst. If triphenylsilanol is added in step (B-i), side reaction with M units takes place to form a by-product $(C_6H_5)_3SiO-SiR^1_3$.

The preferred solvent in step (ii) is an oil which is permitted for use in cosmetics. Suitable solvents (oils) used in step (ii) of embodiment (B) are organic oily ingredients including silicone oils and hydrocarbon oils, preferably volatile siloxane compounds such as octamethyltrisiloxane, decamethyltetrasiloxane, decamethylcyclopentasiloxane, and tristrimethylsiloxymethylsilane, and volatile hydrocarbon compounds such as isododecane, which may be used alone or in admixture. The oil is used in an amount of 10 to 80% by weight. For condensation reaction, a weakly basic catalyst is used. Suitable weakly basic catalysts include sodium hydrogencarbonate and sodium acetate, which may be used alone or in admixture. The weakly basic catalyst is used in an amount of 0.001 to 10% by weight.

Specifically in (B-ii), after the acid is removed at the end of step (B-i), triphenylsilanol and a solvent (or oil) are added to the hydrolytic condensate. Then condensation reaction of the hydrolytic condensate with triphenylsilanol is conducted in the presence of a weakly basic catalyst while heating at 100 to 150° C. under atmospheric or reduced pressure for 2 to 5 hours to remove the alcohol formed and the excess of water. A phenylsilicone resin solution is obtained. Understandably, the solvent (or oil) may be added during hydrolytic condensation reaction of step (i). Since the phenylsilicone resin is solid, it is preferably diluted with a solvent (oil) to form a solution after the completion of reaction. The solvent of step (i) and the solvent of step (ii) may be distilled off after completion of the reaction. The solvent (oil agent) used for dilution may be the same as or different from the solvent of the solvent of step (i) and the solvent of step (ii). The solvent (oil agent) used for dilution may be silicone oil and hydrocarbon oil and the like. Decamethylcyclopentasiloxane, isododecane and octyl p-methoxycinnamate are preferable. When diluted, the solvent (oil) solution should preferably have a phenylsilicone resin concentration of 30 to 70% by weight.

III. Phenylsilicone Resin-Containing Cosmetics

Embodiment III is a cosmetic composition containing the phenylsilicone resin in a concentration of 0.1 to 40% by weight, preferably 0.5 to 20% by weight.

As long as the benefits of the invention are not compromised, optional ingredients other than the phenylsilicone resin may be used alone or in combination and in any suitable amounts in the cosmetic composition. Optional ingredients are exemplified below, but not limited thereto.

Oil

The oil may be either solid, semi-solid, or liquid at room temperature as long as they are permitted for use in cosmetics. Even the oil used in the preparation method or dilution purpose is acceptable. Examples include silicone oils, hydrocarbon oils, ester oils, glyceride oils, naturally occurring animal and plant oils and fats, semi-synthetic oils and fats, higher alcohols, and fluorochemical oils. Exemplary oils illustrated above as the dilution solvent are described herein though redundant.

Examples of the silicone oil used herein include linear or branched organopolysiloxanes ranging from low viscosity to high viscosity such as dimethylpolysiloxane, tristrimethylsiloxymethylsilane, caprylylmethicone, phenyltrimethicone, tetrakistrimethylsiloxysilane, methylphenylpolysiloxane, methylhexylpolysiloxane, methylhydrogenpolysiloxane, and dimethylsiloxane-methylphenylsiloxane copolymers; cyclic organopolysiloxanes such as octamethylcyclotetrasiloxane, decamethylcyclopentasiloxane, dodecamethylcyclohexasiloxane, tetramethyltetrahydrogencyclotetrasiloxane, and tetramethyltetraphenylcyclotetrasiloxane; silicone rubbers such as amino-modified organopolysiloxane, pyrrolidone-modified organopolysiloxane, pyrrolidone carboxylic acid-modified organopolysiloxane, gum-like dimethylpolysiloxane having a high degree of polymerization, gum-like amino-modified organopolysiloxane, gum-like dimethylsiloxane-methylphenylsiloxane copolymers; and silicone gum, silicone gum in cyclic organopolysiloxane, higher alkoxy-modified silicone (e.g., stearoxysilicone), higher fatty acid-modified silicone, alkyl-modified silicone, long chain alkyl-modified silicone, amino acid-modified silicone, fluorine-modified silicone.

Suitable hydrocarbon oils include linear, branched or volatile hydrocarbon oils. Examples include ozokerite, α-olefin oligomers, soft isoparaffin, isododecane, isohexadecane, soft liquid isoparaffin, squalane, synthetic squalane, vegetable squalane, squalene, ceresin, paraffin, paraffin wax, polyethylene wax, polyethylene-polypropylene wax, ethylene/propylene/styrene copolymers, butylene/propylene/styrene copolymers, liquid paraffin, liquid isoparaffin, pristane, polyisobutylene, hydrogenated polyisobutene, microcrystalline wax, and vaseline; higher fatty acids such as lauric acid, myristic acid, palmitic acid, stearic acid, behenic acid, undecylenic acid, oleic acid, linoleic acid, linolenic acid, arachidic acid, eicosapentaenoic acid (EPA), docosahexaenoic acid (DHA), isostearic acid, and 12-hydroxystearic acid.

Examples of the ester oil include diisobutyl adipate, 2-hexyldecyl adipate, di-2-heptylundecyl adipate, N-alkyl glycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyl dodecyl gum ester, oleyl oleate, octyl dodecyl oleate, decyl oleate, neopentyl glycol dioctanoate, neopentyl glycol dicaprilate, triethyl citrate, 2-ethylhexyl succinate, pentyl acetate, ethyl acetate, butyl acetate, isocetyl stearate, butyl stearate, diisopropyl sebacate, di-2-ethylhexyl sebacate, cetyl lactate, myristyl lactate, isononyl isononanoate, isotridecyl isononanoate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, octyl dodecyl myristate, 2-hexyldecyl myristate, myristyl myristate, hexyl decyl dimethyloctanoate, ethyl laurate, hexyl laurate, N-lauroyl-L-glutamic acid 2-octyldodecyl ester, lauroyl sarcosine isopropyl ester, and diisostearyl malate.

Suitable glyceride oils include acetone glyceryl, glyceryl triisooctanoate, glyceryl triisostearate, glyceryl triisopalmitate, glyceryl tribehenate, glyceryl monostearate, glyceryl di-2-heptylundecanoate, glyceryl trimyristate, and diglyceryl myristate isostearate.

Suitable naturally occurring animal and plant oils and semi-synthetic oils include avocado oil, linseed oil, almond oil, insect wax, perilla oil, olive oil, cocoa butter, kapok wax, kaya oil, carnauba wax, liver oil, candelilla wax, purified candelilla wax, beef tallow, neat's foot fat, beef bone fat, hardened beef tallow, persic oil, spermaceti, hardened oil, wheat germ oil, sesame oil, rice germ oil, rice bran oil, sugarcane wax, camellia oil, safflower oil, shea butter, Chinese tung oil, cinnamon oil, jojoba wax, squalane, squalene, shellac wax, turtle oil, soy oil, tea seed oil, evening primrose oil, corn oil, lard, rapeseed oil, Japanese tung oil, rice bran wax, germ oil, horse fat, persic oil, palm oil, palm kernel oil, castor oil, hydrogenated castor oil, castor oil fatty acid methyl ester, sun flower oil, grape oil, bayberry wax, jojoba oil, macadamia nut oil, bees wax, mink oil, meadowfoam oil, cotton seed oil, cotton wax, Japan wax, Japan kernel oil, montan wax, palm oil, hydrogenated palm oil, tri-coconut oil fatty acid glyceride, mutton, peanut oil, lanolin, liquid lanolin, reduced lanolin, lanolin alcohol, hard lanolin, lanolin acetate, lanolin alcohol acetate, isopropyl lanolin fatty acid, polyoxyethylene (POE) lanolin alcohol ether, POE lanolin alcohol acetate, lanolin fatty acid polyethylene glycol, POE hydrogenated lanolin alcohol ether, and egg yolk oil.

Suitable higher alcohols include lauryl alcohol, myristyl alcohol, palmityl alcohol, stearyl alcohol, behenyl alcohol, hexadecyl alcohol, oleyl alcohol, isostearyl alcohol, hexyl dodecanol, octyl dodecanol, cetostearyl alcohol, 2-decyltetradecinol, cholesterol, phytosterol, POE cholesterol ether, monostearyl glycerol ether (batyl alcohol), and monooleyl glyceryl ether (selachyl alcohol).

Suitable fluorochemical oils include perfluoropolyether, perfluorodecalin, and perfluorooctane.

The amount of the oil, if used, is preferably 1 to 98% by weight of the cosmetic composition although the amount varies with a particular form of the composition.

Water

When used, the amount of water is preferably 1 to 95% by weight of the cosmetic composition.

Alcohol

Suitable alcohols include lower alcohols of 2 to 5 carbon atoms, polyhydric alcohols of 2 to 10 carbon atoms, sucrose alcohols, and sterols. Suitable lower alcohols of 2 to 5 carbon atoms include ethanol and isopropanol. Suitable polyhydric alcohols of 2 to 10 carbon atoms include butylene glycol, propylene glycol, dibutylene glycol, and pentylene glycol. Suitable sucrose alcohols include sorbitol and maltose. Suitable sterols include cholesterol, citosterol, phytosterol, and lanosterol. When used, the amount of the alcohol is preferably 0.1 to 98% by weight of the cosmetic composition.

Water-Soluble Thickener

Examples of the water-soluble thickener include water-soluble or water-swellable polymers such as plant-derived polymers, microorganism-derived polymers, animal-derived polymers, starch based polymers, cellulose based polymers, alginic acid based polymers, vinyl based polymers, polyoxyethylene-polyoxypropylene copolymer based polymers, acrylic polymers, and inorganic water-soluble polymers.

Suitable plant-derived polymers include gum Arabic, tragacanth gum, galactan, carob gum, guar gum, karaya gum, carrageenan, pectin, agar, quince seed (marmelo), starch (rice, corn, potato, wheat), algae colloid, and locust bean gum. Suitable microorganism-derived polymers include xanthan gum, dextran, succinoglucan, and pullulan. Suitable animal-derived polymers include collagen, casein, albumin, and gelatin. Suitable starch based polymers include carboxymethyl starch and methyl hydroxypropyl starch. Suitable cellulose based polymers include methyl cellulose, ethyl cellulose, methyl hydroxypropyl cellulose, carboxymethyl cellulose, hydroxymethyl cellulose, hydroxypropyl cellulose, nitrocellulose, cellulose sodium sulfate, sodium carboxymethyl cellulose, crystalline cellulose, and cellulose powder. Suitable alginic acid based polymers include sodium alginate and propylene glycol alginate. Suitable vinyl based polymers include polyvinyl methyl ether and carboxyvinyl polymers. Suitable polyoxyethylene-polyoxypropylene copolymer based polymers include polyoxyethylene polymers, polyoxypropylene polymers, and polyoxyethylene-polyoxypropylene copolymers. Suitable acrylic polymers include sodium polyacrylate, polyethyl acrylate, polyacrylamide, and acryloyl dimethyl taurine salt copolymers. Suitable inorganic water-soluble polymers include bentonite, aluminum magnesium silicate, montmorillonite, beidellite, nontronite, saponite, hectorite, and silicic anhydride. Besides, synthetic water-soluble polymers such as polyethylene imine and cation polymers are also included.

When used, the amount of the thickener is preferably 0.1 to 25% by weight of the cosmetic composition.

Surfactant

Anionic surfactants include fatty acid soaps such as sodium stearate and triethanolamine palmitate, alkyl ether carboxylic acids and salts thereof, condensate salts of amino acids and fatty acids, alkane sulfonic acid salts, alkene sulfonic acid salts, sulfonic acid salts of fatty acid esters, sulfonic acid salts of fatty acid amides, sulfonic acid salts of formalin condensates, alkyl sulfate salts, secondary higher alcohol sulfate salts, alkyl and allyl ether sulfate salts, sulfate salts of fatty acid esters, sulfate salts of fatty acid alkylolamides, sulfate salts of Turkey red oil or the like, alkyl phosphoric acid salts, ether phosphoric acid salts, alkyl allyl ether phosphoric acid salts, amide phosphoric acid salts, N-acyl lactic acid salts, N-acyl sarcosine salts, and N-acylamino acid base surfactants.

Cationic surfactants include amine salts such as alkyl amine salts, polyamine and aminoalcohol fatty acid derivatives, alkyl quaternary ammonium salts, aromatic quaternary ammonium salts, pyridinium salts, and imidazolium salts.

Nonionic surfactants include sorbitan fatty acid esters, glycerol fatty acid esters, polyglycerol fatty acid esters, propylene glycol fatty acid esters, polyethylene glycol fatty acid esters, sucrose fatty acid esters, methyl glucoside fatty acid esters, alkyl polyglucosides, polyoxyethylene alkyl ethers, polyoxypropylene alkyl ethers, polyoxyethylene alkyl phenyl ethers, polyoxyethylene fatty acid esters, polyoxyethylene sorbitan fatty acid esters, polyoxyethylene sorbitol fatty acid esters, polyoxyethylene glycerol fatty acid esters, polyoxyethylene propylene glycol fatty acid esters, polyoxyethylene castor oil, polyoxyethylene hydrogenated castor oil, polyoxyethylene phytostanol ether, polyoxyethylene phytosterol ether, polyoxyethylene cholestanol ether, polyoxyethylene cholesteryl ether, linear or branched organopolysiloxanes containing a polyoxyalkylene or polyglycerol group and alkyl-co-modified organopolysiloxanes thereof (polyoxyalkylene-modified organopolysiloxane, polyglycerol-modified organopolysiloxane, polyoxyalkylene/alkyl-co-modified organopolysiloxane, branched polyglycerol/alkyl-co-modified organopolysiloxane), alkanol amides, sucrose ethers, and sucrose amides. Exemplary surfactants include KSG-210, 240, 310, 320, 330, 340, 320Z, 350Z, 710, 810, 820, 830, 840, 820Z, 850Z, KF-6011, 6013, 6043, 6028, 6038, 6048, 6100, 6104, 6105, 6106 from Shin-Etsu Chemical Co., Ltd.

Ampholytic surfactants include betaine, phosphatidylcholine, amino carboxylic acid salts, imidazoline derivatives, and amidoamine compounds.

Of these, linear or branched organopolysiloxanes having a polyoxyalkylene or polyglycerol chain in the molecule and linear or branched organopolysiloxanes having a polyoxyalkylene or polyglycerol chain (linear or branched organopolysiloxanes having a polyoxyalkylene or polyglycerol group) and alkyl-co-modified organopolysiloxanes thereof (example, a $C_6$-$C_{20}$ long-chain alkyl group in the molecule) are preferred.

It is noted that when the surfactant has a hydrophilic group selected from polyoxyalkylene and polyglycerol groups, the content of the hydrophilic group is preferably 10 to 70% by weight of the molecule.

When used, the amount of the surfactant is preferably 0.1 to 20% by weight, more preferably 0.2 to 10% by weight of the cosmetic composition.

Admixture of Crosslinked Organopolysiloxane Polymer and Liquid Oil

The cosmetic composition may further comprise an admixture of a crosslinked organopolysiloxane polymer and a liquid oil. It is preferred that a crosslinked organopolysiloxane polymer be swollen with a liquid oil by incorporating the liquid oil in an amount of more than its own weight. The liquid oil is typically selected from liquid silicone oils, hydrocarbon oils, ester oils, naturally occurring animal and plant oils, semi-synthetic oils, and fluorochemical oils. Examples include silicone oils having a low viscosity of 0.65 mm$^2$/sec to 100.0 mm$^2$/sec at 25° C., hydrocarbon oils such as liquid paraffin, squalane, isododecane, and isohexadecane, glyceride oils such as trioctanoin, ester oils such as isotridecyl isononanoate, N-acylglutamic acid esters, and lauroyl sarcosine acid esters, and animal and plant oils such as macadamia nut oil. A crosslinker used for the crosslinked organopolysiloxane polymer is preferably a compound having at least two vinyl reactive sites in the molecule and capable of reacting with silicon-bonded hydrogen atom to form a crosslinked structure. Exemplary of the compound having at least two vinyl reactive sites in the molecule are organopolysiloxanes having at least two vinyl groups in the molecule, polyoxyalkylenes having at least two allyl groups in the molecule, polyglycerols having at least two allyl groups in the molecule, and α,ω-alkenyl dienes.

Commercially available examples of the crosslinked organopolysiloxane polymer include KSG-15, KSG-1510, KSG-16, KSG-1610, KSG-18A, KSG-19, KSG-016F, KSG-41A, KSG-42A, KSG-43, KSG-44, KSG-045Z, KSG-210, KSG-310, KSG-320, KSG-330, KSG-340, KSG-320Z, KSG-350Z, KSG-360Z, KSG-710, KSG-810, KSG-820, KSG-840, KSG-820Z, and KSG-850Z from Shin-Etsu Chemical Co., Ltd.

When used, the amount of the admixture of crosslinked organopolysiloxane polymer and liquid oil is preferably 0.1 to 80% by weight, more preferably 1 to 50% by weight of the cosmetic composition.

Film-Forming Agent

A film-forming agent may be added to the cosmetic composition. The film-forming agent is typically selected from among (i) silicone resins, exclusive of the phenylsilicone resin defined above, comprising constituent units: [$R^5_3SiO_{1/2}$], [$R^6_2SiO_{2/2}$], [$R^7SiO_{3/2}$], and [$SiO_{4/2}$] wherein $R^5$, $R^6$ and $R^7$ are each independently a $C_1$-$C_8$ alkyl group, $C_6$-$C_{12}$ aryl group or $C_1$-$C_8$ fluorinated alkyl group, $R^5$, $R^6$ and $R^7$ may be different in the molecule, (ii) linear acrylic-silicone copolymers, and (iii) other silicone resins.

Examples of the silicone resin, exclusive of the phenylsilicone resin, include KF-7312J, KF-7312K, KF-7312T, X-21-5249, X-21-5250, KF-9021, X-21-5595, and X-21-5616 from Shin-Etsu Chemical Co., Ltd.

The linear acrylic-silicone copolymer used herein is not particularly limited as long as it is commonly used in cosmetics. The copolymer may be a block or graft copolymer. The linear acrylic-silicone copolymer may contain in the molecule at least one anionic group selected from pyrrolidinyl, long-chain alkyl, polyoxyalkylene, fluoroalkyl, and carboxyl groups. Examples of the linear acrylic-silicone copolymer include KP-541, KP-543, KP-545, KP-549, KP-550, KP-545L, KP-561P, KP-562P, KP-575, and KP-578 from Shin-Etsu Chemical Co., Ltd.

Examples of the other silicone resin include TSPL-30-ID, TSPL-30-D5, and NBN-30-ID from Shin-Etsu Chemical Co., Ltd.

When used, the amount of the film-forming agent blended is preferably 0.1 to 20% by weight, more preferably 1 to 10% by weight based on the cosmetic composition.

Powder

The powder used herein is not particularly limited with respect to shape (spherical, needle or plate), particle size (fumed, microparticulate, pigment grade), and particle structure (porous or non-porous) as long as it is commonly blended in cosmetics. Examples include inorganic powders, organic powders, surface active metal salt powders, color pigments, pearly pigments, metal powder pigments, tar dyes, and natural dyes.

Suitable inorganic powders include titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, trilithionite, biotite, lepidolite, silicic acid, silicic anhydride, aluminum silicate, magnesium silicate, aluminum magnesium silicate, calcium silicate, barium silicate, strontium silicate, tungstic acid metal salts, hydroxyapatite, vermiculite, gibbsite, bentonite, montmorillonite, hectorite, zeolite, ceramic powder, calcium secondary phosphate, alumina, aluminum hydroxide, boron nitride, and silica.

Suitable organic powders include polyamide powder, polyester powder, polyethylene powder, polypropylene powder, polystyrene powder, polyurethane, benzoguanamine powder, polymethylbenzoguanamine powder, tetrafluoroethylene powder, polymethyl methacrylate powder, cellulose, silk powder, nylon powder, 12 nylon, 6 nylon, silicone powder, styrene-acrylate copolymers, divinylbenzene-styrene copolymers, vinyl resins, urea resins, phenolic resins, fluoro-resins, silicon resins, acrylic resins, melamine resins, epoxy resins, polycarbonate resins, microcrystalline fiber powder, starch powder, and lauroyl lysine.

Suitable surface active metal salt (or metal soap) powders include zinc stearate, aluminum stearate, calcium stearate, magnesium stearate, zinc myristate, magnesium myristate, zinc cetyl phosphate, calcium cetyl phosphate, and zinc sodium cetyl phosphate.

Suitable color pigments include inorganic red pigments such as iron oxide, iron hydroxide, and iron titanate, inorganic brown pigments such as γ-iron oxide, inorganic yellow pigments such as yellow iron oxide and loess, inorganic black pigments such as black iron oxide and carbon black, inorganic purple pigments such as manganese violet and cobalt violet, inorganic green pigments such as chromium hydroxide, chromium oxide, cobalt oxide and cobalt titanate, inorganic blue pigments such as Prussian blue and ultramarine, lake form tar dyes, lake form natural dyes, and synthetic resin powders obtained by combining the foregoing powders.

Suitable pearly pigments include titania-coated mica, bismuth oxychloride, titania-coated bismuth oxychloride, titania-coated talc, argentine, and titania-coated color mica. Suitable metal powder pigments include aluminum powder, copper powder, and stainless steel powder.

Suitable tar dyes include Red #3, Red #104, Red #106, Red #201, Red #202, Red #204, Red #205, Red #220, Red #226, Red #227, Red #228, Red #230, Red #401, Red #505, Yellow #4, Yellow #5, Yellow #202, Yellow #203, Yellow #204, Yellow #401, Blue #1, Blue #2, Blue #201, Blue #404, Green #3, Green #201, Green #204, Green #205, Orange #201, Orange #203, Orange #204, Orange #206, and Orange

207. Suitable natural dyes include carminic acid, laccaic acid, carthamin, brazilin, and crocin.

As long as the benefits of the invention are not compromised, the powder may be used in modified form, for example, composite form of powders, powder treated with ordinary oils, silicone oils, fluorine compounds or surfactants, and powder treated with hydrolyzable silyl groups or alkyl groups having a silicon-bonded hydrogen atom. Also useful are linear and/or branched organopolysiloxanes having a hydrolyzable silyl group and a silicon-bonded hydrogen atom, linear and/or branched organopolysiloxanes having a hydrolyzable silyl group and a silicon-bonded hydrogen atom and co-modified with long-chain alkyl, linear and/or branched organopolysiloxanes having a hydrolyzable silyl group and a silicon-bonded hydrogen atom and co-modified with polyoxyalkylene, and acrylic/silicone copolymers having a hydrolyzable silyl group and a silicon-bonded hydrogen atom.

For example, the swollen form of silicone powder in silicone oil is commercially available as KMP-598, 590, 591 and KFG-016F from Shin-Etsu Chemical Co., Ltd.

A composite form of silicone powder is silicone resin-coated silicone rubber powder. Examples include vinyldimethicone/methiconesilsesquioxane cross polymer, diphenyldimethicone/vinyldiphenyldimethicone/silsesquioxane cross polymer, polysilicone-22, and polysilicone-1 cross polymer, as expressed according to the nomenclature of cosmetic ingredients. They are commercially available under the trade name of KSP-100, 101, 102, 105, 300, 411, and 441 from Shin-Etsu Chemical Co., Ltd.

When used, the amount of powder blended is preferably 0.1 to 99% by weight, more preferably 1 to 70% by weight of the cosmetic composition. When the cosmetic composition is a powdery solid cosmetic, the amount of powder blended is preferably 80 to 99% by weight based on the overall cosmetic composition.

Other additives may be added to the cosmetic composition as long as the benefits of the invention are not compromised. Suitable additives include oil-soluble gelling agents, antiperspirants, UV absorbers, UV absorbing/scattering agents, humectants, preservatives, bactericides, salts, antioxidants, pH adjusting agents, chelating agents, refreshing agents, anti-inflammatory agents, skin improving agents (brightening agent, cell activating agent, anti-skin-roughening agent, blood flow promotor, skin astringent, antiseborrheic agent), vitamins, amino acids, nucleic acids, hormones, hair setting agents, perfumes, and inclusion compounds, which may be used alone or in admixture.

Suitable oil-soluble gelling agents include metal soaps such as aluminum stearate, magnesium stearate, and zinc myristate; amino acid derivatives such as N-lauroyl-L-glutamic acid and α,γ-di-n-butylamine; dextrin fatty acid esters such as dextrin palmitate, dextrin stearate, and dextrin 2-ethylhexanoate palmitate; sucrose fatty acid esters such as sucrose palmitate and sucrose stearate; fructooligosaccharide fatty acid esters such as fructooligosaccharide stearate and fructooligosaccharide 2-ethylhexanoate; benzylidene derivatives of sorbitol such as monobenzylidene sorbitol and dibenzylidene sorbitol; and organo-modified clay minerals such as dimethylbenzyldodecylammonium montmorillonite clay and dimethyldioctadecylammonium montmorillonite clay.

Suitable antiperspirants include aluminum chlorohydrate, aluminum chloride, aluminum sesquichlorohydrate, zirconyl hydroxychloride, aluminum zirconium hydroxychloride, and aluminum zirconium glycine complex.

Suitable UV absorbers include benzoic acid base UV absorbers such as p-aminobenzoic acid, anthranilic acid base UV absorbers such as methyl anthranilate, salicylic acid base UV absorbers such as methyl salicylate, octyl salicylate and trimethylcyclohexyl salicylate, cinnamic acid base UV absorbers such as octyl p-methoxycinnamate, benzophenone base UV absorbers such as 2,4-dihydroxybenzophenone and 2-hydroxy-4-methoxybenzophenone, urocanic acid base UV absorbers such as ethyl urocanate, dibenzoylmethane base UV absorbers such as 4-t-butyl-4'-methoxy-dibenzoylmethane, phenyl benzimidazole sulfonic acid, and triazine derivatives. Suitable UV absorbing/scattering agents include microparticulate titanium oxide, microparticulate iron-containing titanium oxide, microparticulate zinc oxide, microparticulate cerium oxide, and composites thereof, and UV absorbing/scattering powders. Dispersions of UV absorbing/scattering powders in oils are also acceptable. When used, the amount of UV absorber blended is preferably 1 to 30% by weight of the cosmetic composition.

Suitable humectants include glycerol, sorbitol, propylene glycol, dipropylene glycol, 1,3-butylene glycol, pentylene glycol, glucose, xylitol, maltose, polyethylene glycol, hyaluronic acid, chondroitin sulfate, pyrrolidone carboxylate, polyoxyethylene methyl glucoxide, polyoxypropylene methyl glucoxide, egg yolk lecithin, soy lecithin, phosphatidylcholine, phosphatidyl ethanol amine, phosphatidyl serine, phosphatidyl glycerol, phosphatidyl inositol, and sphingophospholipid.

Suitable preservatives include alkyl p-hydroxybenzoates, benzoic acid, sodium benzoate, sorbic acid, potassium sorbate, and phenoxyethanol. Suitable bactericides include benzoic acid, salicylic acid, carbolic acid, sorbic acid, alkyl p-hydroxybenzoates, p-chloro-m-cresol, hexachlorophene, benzalkonium chloride, chlorohexidine chloride, trichlorocarbaniride, photosensitizer, and phenoxyethanol.

Suitable salts include inorganic salts, organic acid salts, amine salts, and amino acid salts. Exemplary inorganic salts include sodium, potassium, magnesium, calcium, aluminum, zirconium and zinc salts of inorganic acids such as hydrochloric acid, sulfuric acid, carbonic acid, and nitric acid. Exemplary organic acid salts include salts of organic acids such as acetic acid, dehydroacetic acid, citric acid, malic acid, succinic acid, ascorbic acid, and stearic acid. Exemplary amine salts and amino acid salts include salts of amines such as triethanolamine, and salts of amino acids such as glutamic acid. In addition, hyaluronic acid, chondroitin sulfate and similar salts, aluminum zirconium glycine complex, and neutralized salts of acid-alkali as used in cosmetic formulation may be used.

Suitable antioxidants include tocopherol, p-t-butylphenol, butyl hydroxyanisole, dibutylhydroxytoluene, and phytic acid. Suitable pH adjusting agents include lactic acid, citric acid, glycolic acid, succinic acid, tartaric acid, dl-malic acid, potassium carbonate, sodium hydrogencarbonate, and ammonium hydrogencarbonate. Suitable chelating agents include alanine, sodium salt of EDTA, sodium polyphosphate, sodium metaphosphate, and phosphoric acid. Suitable refreshing agents include L-menthol and camphor. Suitable anti-inflammatory agents include arantoin, glycyrrhizic acid and salts thereof, glycyrrhetinic acid, stearyl glycyrrhetinate, tranexamic acid and azulene.

Suitable skin improving agents include brightening agents such as placenta extract, arbutin, glutathione and Saxifrage stolonifera extract; cell activating agents such as royal jelly, photosensitizer, cholesterol derivatives, bovine blood extract; anti-skin-roughening agents; blood flow promotors such as nonanoic acid vanillylamide, benzyl nicotinate, β-butoxyethyl nicotinate, capsaicin, zingerone, cantharides tincture, ichthammol, caffeine, tannic acid, α-borneol, nicotinic acid tocopherol, inositol hexanicotinate, cyclandelate, cinnarizine, tolazoline, acetylcholine, verapamil, cepharanthine, and γ-oryzanol; skin astringents such as zinc oxide and tannic acid; antiseborrheic agents such as sulfur and thianthrol.

Suitable vitamins include vitamin A species such as vitamin A oil, retinol, retinol acetate, and retinol palmitate; vitamin B species, for example, vitamin B2 species such as riboflavin, riboflavin butyrate, and flavin adenine nucleotide, vitamin B6 species such as pyridoxine hydrochloride, pyridoxine dioctanoate, and pyridoxine tripalmitate, vitamin B12 and derivatives thereof, vitamin B15 and derivatives thereof, and biotin; vitamin C species such as L-ascorbic acid, L-ascorbic acid dipalmitic acid ester, sodium L-ascorbic acid-2-sulfate, and dipotassium L-ascorbic acid phosphoric acid diester; vitamin D species such as ergocalciferol and cholecalciferol; vitamin E species such as α-tocopherol, β-tocopherol, γ-tocopherol, dl-α-tocopherol acetate, dl-α-tocopherol nicotinate, and dl-α-tocopherol succinate; vitamin H; vitamin P; nicotinic acids such as nicotinic acid, benzyl nicotinate and nicotinic acid amide; and pantothenic acids such as calcium pantothenate, D-pantothenyl alcohol, pantothenyl ethyl ether, and acetylpantothenyl ethyl ether.

Suitable amino acids include glycine, valine, leucine, isoleucine, serine, threonine, phenylalanine, arginine, lysine, aspartic acid, glutamic acid, cystine, cysteine, methionine, and tryptophan. Typical of the nucleic acid is deoxyribonucleic acid. Suitable hormones include estradiol and ethenylestradiol.

Suitable hair setting agents include ampholytic, anionic, cationic, and nonionic polymers. Useful examples include polyvinyl pyrrolidone base polymers such as polyvinyl pyrrolidone and vinyl pyrrolidone-vinyl acetate copolymers, acidic vinyl ether base polymers such as methyl vinyl ether-maleic anhydride alkyl half ester copolymers, acidic vinyl acetate base polymers such as vinyl acetate-crotonic acid copolymers, acidic acrylic polymers such as (meth) acrylic acid/alkyl (meth)acrylate copolymers, (meth)acrylic acid/alkyl (meth)acrylate/alkyl acrylamide copolymers, and ampholytic acrylic polymers such as N-methacryloylethyl-N,N-dimethylammonium/α-N-methylcarboxybetain/alkyl (meth)acrylate copolymers, hydroxypropyl (meth)acrylate/butylamino ethyl methacrylate/acrylic acid octylamide copolymers. Also included are naturally occurring polymers such as cellulose and derivatives thereof, keratin, collagen and derivatives thereof.

While the cosmetic composition is not particularly limited in form or state, it may be aqueous, oily, water-in-oil emulsion, oil-in-water emulsion, non-aqueous emulsion, multi-emulsion such as W/O/W or O/W/O, suspension, paste or solid.

While the cosmetic composition is not particularly limited in type, it may be any of skin care cosmetics, hair care cosmetics, make-up cosmetics, UV protective cosmetics, and antiperspirants. Suitable skin care cosmetics include toilet water, lotion, milky lotion, cream, cleansing, pack, oil liquid, massage agent, esthetic liquid, esthetic oil, hand cream, lip cream, and wrinkle concealer. Suitable hair care cosmetics include shampoo, rinse, treatment, hair cream, cuticle coat and setting agent. Suitable make-up cosmetics include make-up foundation, concealer, powder, powder foundation, liquid foundation, cream foundation, oily foundation, blusher, eye shadow, mascara, eye liner, eye brow, lipstick, and nail care products. Suitable UV protective cosmetics include sun cutting or sun care oil, sun cutting milky lotion, sun cutting cream, and sun cutting lotion.

EXAMPLE

Examples and Comparative Examples are shown below for further illustrating the invention although the invention is not limited thereto. All percents (%) are by weight unless otherwise stated. IPA stands for isopropyl alcohol, and Mw for weight average molecular weight.

Example 1

A reactor was charged with 70 g of hexamethyldisiloxane, 210 g of triethoxyphenylsilane, 100 g of ethyl polysilicate having a $SiO_2$ content of 40%, and 110 g of IPA. Methanesulfonic acid, 2.2 g, was added to the reactor, which was cooled to 10-20° C. With stirring, 112 g of water was added dropwise. At the end of dropwise addition, the solution was heated at 40-60° C. for 5 hours to conduct hydrolytic condensation reaction, yielding a silicone resin solution.

Next, 3.5 g of 25% sodium hydroxide aqueous solution and 0.5 g of calcium carbonate were added to the solution to neutralize the acid, after which 22 g of triphenylsilanol, 1.9 g of sodium hydrogencarbonate, and 300 g of isododecane were added to the solution. The solution was heated at 100° C. for 3 hours, then at 130° C. for 2 hours to remove the ethanol formed and excess of water, after which it was cooled. This was followed by distillation in vacuum, controlled dilution with isododecane to a silicone resin concentration of 50%, and filtration, yielding a 50% isododecane solution of a silicone resin having a Mw of 2,950 and consisting of $(C_6H_5)_3SiO_{1/2}$ units, $(CH_3)_3SiO_{1/2}$ units, $(C_6H_5)SiO_{3/2}$ units and $SiO_{4/2}$ units in a molar ratio of 0.03:0.36:0.33:0.28. A film of this silicone resin had a refractive index of 1.506.

Example 2

A reactor was charged with 70 g of hexamethyldisiloxane, 210 g of triethoxyphenylsilane, 100 g of ethyl polysilicate having a $SiO_2$ content of 40%, and 110 g of IPA. Methanesulfonic acid, 2.2 g, was added to the reactor, which was cooled to 10-20° C. With stirring, 112 g of water was added dropwise. At the end of dropwise addition, the solution was heated at 40-60° C. for 5 hours to conduct hydrolytic condensation reaction, yielding a silicone resin solution.

Next, 3.5 g of 25% sodium hydroxide aqueous solution and 0.5 g of calcium carbonate were added to the solution to neutralize the acid, after which 22 g of triphenylsilanol, 1.9 g of sodium acetate, and 300 g of isododecane were added to the solution. The solution was heated at 100° C. for 3 hours, then at 130° C. for 2 hours to remove the ethanol formed and excess of water, after which it was cooled. This was followed by distillation in vacuum, controlled dilution with isododecane to a silicone resin concentration of 50%, and filtration, yielding a 50% isododecane solution of a silicone resin having a Mw of 2,950 and consisting of $(C_6H_5)_3SiO_{1/2}$ units, $(CH_3)_3SiO_{1/2}$ units, $(C_6H_5)SiO_{3/2}$ units and $SiO_{4/2}$ units in a molar ratio of 0.03:0.36:0.33:0.28. A film of this silicone resin had a refractive index of 1.506.

Example 3

A reactor was charged with 41 g of hexamethyldisiloxane, 23 g of diethoxydiphenylsilane, 48 g of triethoxyphenylsilane, 100 g of ethyl polysilicate having a $SiO_2$ content of 40%, and 54 g of IPA. Methanesulfonic acid, 1.1 g, was added to the reactor, which was cooled to 10-20° C. With stirring, 51.5 g of water was added dropwise. At the end of dropwise addition, the solution was heated at 40-60° C. for 5 hours to conduct hydrolytic condensation reaction, yielding a silicone resin solution.

Next, 1.75 g of 25% sodium hydroxide aqueous solution and 0.25 g of calcium carbonate were added to the solution to neutralize the acid, after which 29.5 g of triphenylsilanol, 0.95 g of sodium hydrogencarbonate, and 150 g of isododecane were added to the solution. The solution was heated at 100° C. for 3 hours, then at 130° C. for 2 hours to remove the ethanol formed and excess of water, after which it was cooled. This was followed by distillation in vacuum, controlled dilution with isododecane to a silicone resin concentration of 50%, and filtration, yielding a 50% isododecane solution of a silicone resin having a Mw of 3,500 and consisting of $(C_6H_5)_3SiO_{1/2}$ units, $(CH_3)_3SiO_{1/2}$ units, $(C_6H_5)_2SiO_{2/2}$ units, $(C_6H_5)SiO_{3/2}$ units and $SiO_{4/2}$ units in a molar ratio of 0.07:0.33:0.06:0.11:0.43. A film of this silicone resin had a refractive index of 1.501.

Example 4

A reactor was charged with 41 g of hexamethyldisiloxane, 23 g of diethoxydiphenylsilane, 24 g of triethoxyphenylsilane, 100 g of ethyl polysilicate having a $SiO_2$ content of 40%, and 54 g of IPA. Methanesulfonic acid, 1.1 g, was added to the reactor, which was cooled to 10-20° C. With stirring, 45 g of water was added dropwise. At the end of dropwise addition, the solution was heated at 40-60° C. for 5 hours to conduct hydrolytic condensation reaction, yielding a silicone resin solution.

Next, 1.75 g of 25% sodium hydroxide aqueous solution and 0.25 g of calcium carbonate were added to the solution to neutralize the acid, after which 29.5 g of triphenylsilanol, 0.95 g of sodium hydrogencarbonate, and 150 g of isododecane were added to the solution. The solution was heated at 100° C. for 3 hours, then at 130° C. for 2 hours to remove the ethanol formed and excess of water, after which it was cooled. This was followed by distillation in vacuum, controlled dilution with octamethylcyclotetrasiloxane to a silicone resin concentration of 50%, and filtration, yielding a 50% isododecane solution of a silicone resin having a Mw of 3,270 and consisting of $(C_6H_5)_3SiO_{1/2}$ units, $(CH_3)_3SiO_{1/2}$ units, $(C_6H_5)_2SiO_{2/2}$ units, $(C_6H_5)SiO_{3/2}$ units and $SiO_{4/2}$ units in a molar ratio of 0.07:0.35:0.06:0.06:0.46. A film of this silicone resin had a refractive index of 1.492.

Example 5

A reactor was charged with 54 g of hexamethyldisiloxane, 170 g of triethoxyphenylsilane, 61 g of ethyl polysilicate having a $SiO_2$ content of 40%, and 110 g of IPA. Methanesulfonic acid, 2.2 g, was added to the reactor, which was cooled to 10-20° C. With stirring, 80 g of water was added dropwise. At the end of dropwise addition, the solution was heated at 40-60° C. for 5 hours to conduct hydrolytic condensation reaction, yielding a silicone resin solution.

Next, 3.5 g of 25% sodium hydroxide aqueous solution and 0.5 g of calcium carbonate were added to the solution to neutralize the acid, after which 14 g of triphenylsilanol, 1.9 g of sodium hydrogencarbonate and 200 g of isododecane were added to the solution. The solution was heated at 100° C. for 3 hours, then at 130° C. for 2 hours to remove the ethanol formed and excess of water, after which it was cooled. This was followed by distillation in vacuum, controlled dilution with isododecane to a silicone resin concentration of 50%, and filtration, yielding a 50% isododecane solution of a silicone resin having a Mw of 2,930 and consisting of $(C_6H_5)_3SiO_{1/2}$ units, $(CH_3)_3SiO_{1/2}$ units, $(C_6H_5)SiO_{3/2}$ units and $SiO_{4/2}$ units in a molar ratio of 0.03:0.38:0.36:0.23. A film of this silicone resin had a refractive index of 1.511.

Example 6

A reactor was charged with 60 g of hexamethyldisiloxane, 170 g of triethoxyphenylsilane, 61 g of ethyl polysilicate having a $SiO_2$ content of 40%, and 110 g of IPA. Methanesulfonic acid, 2.2 g, was added to the reactor, which was cooled to 10-20° C. With stirring, 100 g of water was added dropwise. At the end of dropwise addition, the solution was heated at 40-60° C. for 5 hours to conduct hydrolytic condensation reaction, yielding a silicone resin solution.

Next, 3.5 g of 25% sodium hydroxide aqueous solution and 0.5 g of calcium carbonate were added to the solution to neutralize the acid, after which 1.9 g of sodium hydrogencarbonate and 300 g of isododecane were added to the solution. The solution was heated at 100° C. for 3 hours, then at 130° C. for 2 hours to remove the ethanol formed and excess of water, after which it was cooled. This was followed by distillation in vacuum, controlled dilution with isododecane to a silicone resin concentration of 50%, and filtration, yielding a 50% isododecane solution of a silicone resin having a Mw of 3,410 and consisting of $(CH_3)_3SiO_{1/2}$ units, $(C_6H_5)SiO_{3/2}$ units and $SiO_{4/2}$ units in a molar ratio of 0.42:0.35:0.23. A film of this silicone resin had a refractive index of 1.488.

Example 7

A reactor was charged with 60 g of hexamethyldisiloxane, 220 g of triethoxyphenylsilane, 61 g of ethyl polysilicate having a $SiO_2$ content of 40%, and 110 g of IPA. Methanesulfonic acid, 2.2 g, was added to the reactor, which was cooled to 10-20° C. With stirring, 100 g of water was added dropwise. At the end of dropwise addition, the solution was heated at 40-60° C. for 5 hours to conduct hydrolytic condensation reaction, yielding a silicone resin solution.

Next, 3.5 g of 25% sodium hydroxide aqueous solution and 0.5 g of calcium carbonate were added to the solution to neutralize the acid, after which 1.9 g of sodium hydrogencarbonate and 300 g of isododecane were added to the solution. The solution was heated at 100° C. for 3 hours, then at 130° C. for 2 hours to remove the ethanol formed and excess of water, after which it was cooled. This was followed by distillation in vacuum, controlled dilution with isododecane to a silicone resin concentration of 50%, and filtration, yielding a 50% isododecane solution of a silicone resin having a Mw of 3,900 and consisting of $(CH_3)_3SiO_{1/2}$ units, $(C_6H_5)SiO_{3/2}$ units and $SiO_{4/2}$ units in a molar ratio of 0.38:0.41:0.21. A film of this silicone resin had a refractive index of 1.503.

Example 8

A reactor was charged with 54 g of hexamethyldisiloxane, 220 g of triethoxyphenylsilane, 61 g of ethyl polysilicate having a $SiO_2$ content of 40%, and 110 g of IPA. Methanesulfonic acid, 2.2 g, was added to the reactor, which was cooled to 10-20° C. With stirring, 100 g of water was added dropwise. At the end of dropwise addition, the solution was heated at 40-60° C. for 5 hours to conduct hydrolytic condensation reaction, yielding a silicone resin solution.

Next, 3.5 g of 25% sodium hydroxide aqueous solution and 0.5 g of calcium carbonate were added to the solution to neutralize the acid, after which 1.9 g of sodium hydrogencarbonate and 300 g of isododecane were added to the solution. The solution was heated at 100° C. for 3 hours, then at 130° C. for 2 hours to remove the ethanol formed and excess of water, after which it was cooled. This was followed by distillation in vacuum, controlled dilution with isododecane to a silicone resin concentration of 50%, and filtration, yielding a 50% isododecane solution of a silicone resin having a Mw of 4,510 and consisting of $(CH_3)_3SiO_{1/2}$ units, $(C_6H_5)SiO_{3/2}$ units and $SiO_{4/2}$ units in a molar ratio of 0.35:0.43:0.22.

A film of this silicone resin had a refractive index of 1.510.

Comparative Example 1

A reactor was charged with 38 g of hexamethyldisiloxane, 101 g of triethoxyphenylsilane, and 55 g of IPA. Methanesulfonic acid, 1.1 g, was added to the reactor, which was cooled to 10-20° C. With stirring, 40 g of water was added dropwise. At the end of dropwise addition, the solution was heated at 40-60° C. for 5 hours to conduct hydrolytic condensation reaction, yielding a silicone resin solution.

Next, 1.75 g of 25% sodium hydroxide aqueous solution and 0.25 g of calcium carbonate were added to the solution to neutralize the acid, after which 0.95 g of sodium hydrogencarbonate and 100 g of isododecane were added to the solution. The solution was heated at 130° C. to remove the ethanol formed and excess of water, after which it was cooled. This was followed by distillation in vacuum, controlled dilution with isododecane to a silicone resin concentration of 50%, and filtration, yielding a 50% isododecane solution of a silicone resin having a Mw of 1,360 and consisting of $(CH_3)_3SiO_{1/2}$ units and $(C_6H_5)SiO_{3/2}$ units in a molar ratio of 0.56:0.44. Because of high viscosity liquid, no film could be formed, and a refractive index was unmeasurable.

Comparative Example 2

A reactor was charged with 18 g of hexamethyldisiloxane, 180 g of triethoxyphenylsilane, and 55 g of IPA. Methanesulfonic acid, 1.1 g, was added to the reactor, which was cooled to 10-20° C. With stirring, 65 g of water was added dropwise. At the end of dropwise addition, the solution was heated at 40-60° C. for 5 hours to conduct hydrolytic condensation reaction, yielding a silicone resin solution.

Next, 1.75 g of 25% sodium hydroxide aqueous solution and 0.25 g of calcium carbonate were added to the solution to neutralize the acid, after which 0.95 g of sodium hydrogencarbonate and 100 g of isododecane were added to the solution. The solution was heated at 130° C. to remove the ethanol formed and excess of water, after which it was cooled. Since the silicone resin did not dissolve in isododecane, the liquid was white turbid and could not be filtered. Thus a refractive index was unmeasurable.

It is noted that the silicone resin prior to filtration had a Mw of 4,310 and consisted of $(CH_3)_3SiO_{1/2}$ units and $(C_6H_5)SiO_{3/2}$ units in a molar ratio of 0.25:0.75.

Comparative Example 3

A reactor was charged with 42 g of hexamethyldisiloxane, 100 g of triethoxyphenylsilane, 140 g of ethyl polysilicate having a $SiO_2$ content of 40%, and 110 g of IPA. Methanesulfonic acid, 1.1 g, was added to the reactor, which was cooled to 10-20° C. With stirring, 55 g of water was added dropwise. At the end of dropwise addition, the solution was heated at 40-60° C. for 5 hours to conduct hydrolytic condensation reaction, yielding a silicone resin solution.

Next, 1.75 g of 25% sodium hydroxide aqueous solution and 0.25 g of calcium carbonate were added to the solution to neutralize the acid, after which 0.95 g of sodium hydrogencarbonate and 100 g of isododecane were added to the solution. The solution was heated at 130° C. to remove the ethanol formed and excess of water, after which it was cooled. This was followed by distillation in vacuum, controlled dilution with isododecane to a silicone resin concentration of 50%, and filtration, yielding a 50% isododecane solution of a silicone resin having a Mw of 10,160 and consisting of $(CH_3)_3SiO_{1/2}$ units, $(C_6H_5)SiO_3$a units and $SiO_{4/2}$ units in a molar ratio of 0.29:0.20:0.51. A film of this silicone resin was too brittle to measure a refractive index.

Comparative Example 4

A reactor was charged with 75 g of hexamethyldisiloxane, 210 g of ethyl polysilicate having a $SiO_2$ content of 40%, and 110 g of IPA. Methanesulfonic acid, 1.1 g, was added to the reactor, which was cooled to 10-20° C. With stirring, 55 g of water was added dropwise. At the end of dropwise addition, the solution was heated at 40-60° C. for 5 hours to conduct hydrolytic condensation reaction, yielding a silicone resin solution.

Next, 1.75 g of 25% sodium hydroxide aqueous solution and 0.25 g of calcium carbonate were added to the solution to neutralize the acid, after which 200 g of isododecane was added to the solution. The solution was heated at 130° C. to remove the ethanol formed and excess of water, after which it was cooled. This was followed by distillation in vacuum, controlled dilution with isododecane to a silicone resin concentration of 50%, and filtration, yielding a 50% isododecane solution of a silicone resin having a Mw of 5,220 and consisting of $(CH_3)_3SiO_{1/2}$ units and $SiO_{4/2}$ units in a molar ratio of 0.40:0.60. A film of this silicone resin was too brittle to measure a refractive index.

Comparative Example 5

A reactor was charged with 50 g of hexamethyldisiloxane, 210 g of triethoxyphenylsilane, 100 g of ethyl polysilicate having a $SiO_2$ content of 40%, and 53 g of IPA. Methanesulfonic acid, 2.2 g, was added to the reactor, which was cooled to 10-20° C. With stirring, 112 g of water was added dropwise. At the end of dropwise addition, the solution was heated at 40-60° C. for 5 hours to conduct hydrolytic condensation reaction, yielding a silicone resin solution.

Next, 3.5 g of 25% sodium hydroxide aqueous solution and 0.5 g of calcium carbonate were added to the solution to neutralize the acid, after which 7.5 g of triphenylsilanol, 1.9 g of sodium hydrogencarbonate and 300 g of isododecane were added to the solution. The solution was heated at 100° C. for 3 hours, then at 130° C. for 2 hours to remove the ethanol formed and excess of water, after which it was cooled. Since the silicone resin did not dissolve in isododecane, the liquid was white turbid and could not be filtered. Thus a refractive index was unmeasurable.

It is noted that the silicone resin prior to filtration had a Mw of 8,120 and consisted of $(C_6H_5)_3SiO_{1/2}$ units, $(CH_3)_3SiO_{1/2}$ units, $(C_6H_5)SiO_{3/2}$ units, and $SiO_{4/2}$ units in a molar ratio of 0.01:0.30:0.37:0.32.

Measurement methods are described below.

Mw: measured versus polystyrene standards by gel permeation chromatography (GPC) using an analyzer of Tosoh Corp.

Molar ratio of constituent units: computed from Si-NMR (JEOL Ltd.)

Refractive index: measured by removing the solvent from a silicone resin solution, to form a film having a thickness of about 1 mm, and analyzing the film at a temperature of 25° C. by means of a refractometer Abbemat (Anton Paar GmbH).

Table 1 tabulates the Mw, molar ratio of constituent units, and phenol content of the silicone resins obtained in Examples as well as the refractive index of their film.

TABLE 1

| | | Mw | Composition (molar ratio) | Phenyl content (%) | Refractive index |
|---|---|---|---|---|---|
| Example | 1 | 2,950 | MΦ/M/TΦ/Q = 0.03/0.36/0.33/0.28 | 35 | 1.506 |
| | 2 | 2,950 | MΦ/M/TΦ/Q = 0.03/0.36/0.33/0.28 | 35 | 1.506 |
| | 3 | 3,500 | MΦ/M/DΦ/TΦ/Q = 0.07/0.33/0.06/0.11/0.43 | 35 | 1.501 |
| | 4 | 3,270 | MΦ/M/DΦ/TΦ/Q = 0.07/0.35/0.06/0.06/0.46 | 32 | 1.492 |
| | 5 | 2,930 | MΦ/M/TΦ/Q = 0.03/0.38/0.36/0.23 | 36 | 1.511 |
| | 6 | 3,410 | M/TΦ/Q = 0.42/0.35/0.23 | 31 | 1.488 |
| | 7 | 3,900 | M/TΦ/Q = 0.38/0.41/0.21 | 35 | 1.503 |
| | 8 | 4,510 | M/TΦ/Q = 0.35/0.43/0.22 | 36 | 1.510 |
| Comparative Example | 1 | 1,360 | M/TΦ = 0.56/0.44 | 35 | — |
| | 2 | 4,310 | M/TΦ = 0.25/0.75 | 50 | — |
| | 3 | 10,160 | M/TΦ/Q = 0.29/0.20/0.51 | 21 | — |
| | 4 | 5,220 | M/Q = 0.40/0.60 | 0 | — |
| | 5 | 8,120 | MΦ/M/TΦ/Q = 0.01/0.30/0.37/0.32 | 35 | — |

MΦ: [(C$_6$H$_5$)$_3$SiO$_{1/2}$]
M: [(CH$_3$)$_3$SiO$_{1/2}$]
DΦ: [(C$_6$H$_5$)$_2$SiO$_{2/2}$]
TΦ: [(C$_6$H$_5$)SiO$_{3/2}$]
Q: [SiO$_{4/2}$]

Reference Example 1

A reactor was charged with 70 g of hexamethyldisiloxane, 22 g of triphenylsilanol, 210 g of triethoxyphenylsilane, 100 g of ethyl polysilicate having a SiO$_2$ content of 40%, and 110 g of IPA. Methanesulfonic acid, 2.2 g, was added to the reactor, which was cooled to 10-20° C. With stirring, 112 g of water was added dropwise. At the end of dropwise addition, the solution was heated at 40-60° C. for 5 hours to conduct hydrolytic condensation reaction, yielding a silicone resin solution.

Next, 3.5 g of 25% sodium hydroxide aqueous solution and 0.5 g of calcium carbonate were added to the solution to neutralize the acid, after which 1.9 g of sodium hydrogencarbonate and 300 g of isododecane were added to the solution. The solution was heated at 100° C. for 3 hours, then at 130° C. for 2 hours to remove the ethanol formed and excess of water, after which it was cooled. By-products formed, after which the procedure was interrupted.

Reference Example 2

A reactor was charged with 70 g of hexamethyldisiloxane, 210 g of triethoxyphenylsilane, 100 g of ethyl polysilicate having a SiO$_2$ content of 40%, and 110 g of IPA. Methanesulfonic acid, 2.2 g, was added to the reactor, which was cooled to 10-20° C. With stirring, 112 g of water was added dropwise. At the end of dropwise addition, the solution was heated at 40-60° C. for 5 hours to conduct hydrolytic condensation reaction, yielding a silicone resin solution.

Next, 3.5 g of 25% sodium hydroxide aqueous solution and 0.5 g of calcium carbonate were added to the solution to neutralize the acid, after which 22 g of triphenylsilanol and 300 g of isododecane were added to the solution. The solution was heated at 100° C. for 3 hours, then at 130° C. for 2 hours to remove the ethanol formed and excess of water, after which it was cooled. The procedure was interrupted because triphenylsilanol did not react.

In preparing a silicone resin having compositional formula (1) wherein a is 0.01 to 0.2, the following was confirmed.

Example 1 and Reference Example 1 demonstrate that if triphenylsilanol is initially charged, by-products form during hydrolysis. It is thus recommended to add triphenylsilanol at the end of hydrolysis.

Examples 1, 2 and Reference Example 2 demonstrate that sodium hydrogencarbonate and sodium acetate are effective as the reaction catalyst for triphenylsilanol.

A film was formed by evaporating off the solvent from each of the silicone resin solutions obtained in Examples. The film was evaluated for outer appearance, stickiness and brittleness by friction. The results are shown in Table 2.

TABLE 2

| | | Outer appearance | Stickiness | Brittleness |
|---|---|---|---|---|
| Example | 1 | uniform continuous film | nil | nil |
| | 2 | uniform continuous film | nil | nil |
| | 3 | uniform continuous film | nil | nil |
| | 4 | uniform continuous film | nil | nil |
| | 5 | uniform continuous film | nil | nil |
| | 6 | uniform continuous film | nil | nil |
| | 7 | uniform continuous film | nil | nil |
| | 8 | uniform continuous film | nil | nil |
| Comparative Example | 1 | high viscosity liquid | sticky | — |
| | 2 | — | — | — |
| | 3 | crazing | nil | brittle |
| | 4 | crazing | nil | brittle |
| | 5 | — | — | — |

All the silicone resins of Examples 1 to 8 formed a uniform continuous film which was neither sticky nor brittle. The silicone resin of Comparative Example 1 was a high viscosity liquid. The silicone resin of Comparative Example 2 did not dissolve in isododecane. The silicone resins of Comparative Examples 3 and 4 formed a hard film which was non-sticky, crazed, and was so brittle that it was readily broken by friction. The silicone resin of Comparative Example 5 did not dissolve in isododecane.

In a compatibility test, the solvent was removed from each of the silicone resin solutions of Examples. The silicone resin was examined for compatibility with various oils (decamethylcyclopentasiloxane, isododecane, and octyl p-methoxycinnamate), by dissolving the resin in an oil to a silicone resin concentration of 50% in an oven at 70° C. The resin was rated "○" for soluble, "Δ" for slightly turbid, and "X" for insoluble. The ratings ○ and Δ are acceptable.

TABLE 3

|  |  | Decamethylcyclo-pentasiloxane | Isododecane | Octyl p-methoxycinnamate |
|---|---|---|---|---|
| Example | 1 | ○ | ○ | ○ |
|  | 2 | ○ | ○ | ○ |
|  | 3 | Δ | ○ | ○ |
|  | 4 | ○ | ○ | ○ |
|  | 5 | ○ | ○ | ○ |
|  | 6 | ○ | ○ | ○ |
|  | 7 | ○ | ○ | ○ |
|  | 8 | ○ | ○ | ○ |
| Comparative Example | 1 | ○ | ○ | ○ |
|  | 2 | X | X | — |
|  | 3 | ○ | ○ | ○ |
|  | 4 | ○ | ○ | X |
|  | 5 | X | X | — |

In another compatibility test, the 50% silicone resin solution obtained in Example was examined for compatibility with various UV absorbers by adding a UV absorber (A), (B) or (C) in an amount of 10% to the 50% silicone resin solution. The result was rated "○" for soluble, "Δ" for slightly turbid, and "X" for insoluble. The ratings ○ and Δ are acceptable.

Notably, the silicone resins of Comparative Examples 2 and 5 were not tested for solubility in octyl p-methoxycinnamate.

TABLE 4

|  |  | (A) octyl p-methoxycinnamate (cinnamic acid base UV absorber) | (B) 2-hydroxy-4-methoxy-benzophenone (benzophenone base UV absorber) | (C) 4-t-butyl-4'-methoxy-dibenzoylmethane (dibenzoylmethane base UV absorber) |
|---|---|---|---|---|
| Example | 1 | ○ | ○ | ○ |
|  | 2 | ○ | ○ | ○ |
|  | 3 | ○ | ○ | ○ |
|  | 4 | ○ | ○ | Δ |
|  | 5 | ○ | ○ | ○ |
|  | 6 | ○ | ○ | Δ |
|  | 7 | ○ | ○ | ○ |
|  | 8 | ○ | ○ | ○ |
| Comparative Example | 1 | ○ | ○ | ○ |
|  | 2 | — | — | — |
|  | 3 | ○ | X | X |
|  | 4 | ○ | X | X |
|  | 5 | — | — | — |

Notably, Comparative Examples 2 and 5 were not tested because the silicone resins did not dissolve in isododecane.

Water Resistance Test

Using the silicone resin solution obtained in Example, a sun cutting cream was prepared in accordance with the following formulation and preparation method. The sun cutting cream was evaluated for water resistance.

| | Formulation | Amount (%) |
|---|---|---|
| 1. | Crosslinked polyether-modified silicone *1 | 3.5 |
| 2. | Crosslinked dimethylpolysiloxane *2 | 3.0 |
| 3. | Alkyl-modified branched polyether-modified silicone *3 | 0.5 |
| 4. | Silicone resin solution of each Example | 10.0 |
| 5. | Isododecane | 1.5 |
| 6. | Octyl p-methoxycinnamate | 7.5 |
| 7. | 1,3-Butylene glycol | 5.5 |
| 8. | Sodium citrate | 0.2 |
| 9. | Sodium chloride | 0.5 |
| 10. | Purified water | 67.8 |
| | Total | 100.0 |

*1 KSG-240 by Shin-Etsu Chemical Co., Ltd.
*2 KSG-18A by Shin-Etsu Chemical Co., Ltd.
*3 KF-6038 by Shin-Etsu Chemical Co., Ltd.

Preparation of Cosmetic Composition

A sun cutting cream was prepared by step A of mixing ingredients 1 to 6 until uniform, step B of mixing ingredients 7 to 10 until uniform, and step C of adding B to A and emulsifying.

The sun cutting cream was coated and spread over a quartz plate, and measured for transmittance (%) by means of an analyzer UV-2000SSPF (Labsphere). The cream on the quartz plate was immersed in water for 40 minutes, after which transmittance was measured again. From the initial transmittance and transmittance after 40 min, the resistance of UV protective effect against water was evaluated, with the results shown in Table 5.

TABLE 5

|  |  | Initial transmittance | Transmittance after 40 min | Difference |
|---|---|---|---|---|
| Example | 1 | 7% | 8% | 1% |
|  | 2 | 7% | 8% | 1% |
|  | 3 | 7% | 8% | 1% |
|  | 4 | 9% | 12% | 3% |
|  | 5 | 6% | 7% | 1% |
|  | 6 | 10% | 13% | 3% |
|  | 7 | 7% | 8% | 1% |
|  | 8 | 7% | 8% | 1% |
| Comparative Example | 1 | 20% | 35% | 15% |
|  | 2 | — | — | — |
|  | 3 | 29% | 36% | 7% |
|  | 4 | 27% | 35% | 8% |
|  | 5 | — | — | — |

The phenylsilicone resin having a high phenyl content shows improved water resistance of UV protective effect because it is highly compatible with octyl p-methoxycinnamate which is effectively retained within a film.

Notably, Comparative Examples 2 and 5 were not tested because the silicone resins did not dissolve in isododecane.

Examples 9, 10 and Comparative Examples 6, 7

Evaluation of Feel on Use of Cosmetics, Secondary Transfer-Preventing Effect

Using the silicone resin solution obtained in Example, an emulsion type cream foundation was prepared in accordance with the following formulation and preparation method. The cream foundation was evaluated by the following tests.

TABLE 6

| | | | Example | | Comparative Example | |
|---|---|---|---|---|---|---|
| No. | Formulation (%) | | 9 | 10 | 6 | 7 |
| 1 | Crosslinked polyether-modified silicone *1 | | 5.0 | 5.0 | 5.0 | 5.0 |
| 2 | Crosslinked dimethylpolysiloxane *2 | | 6.0 | 6.0 | 6.0 | 6.0 |
| 3 | Polyether-modified silicone *3 | | 1.0 | 1.0 | 1.0 | 1.0 |
| 4 | Dimethylpolysiloxane *4 | | 2.0 | 2.0 | 2.0 | 2.0 |
| 5 | Decamethylcyclopentasiloxane | | 6.3 | 6.3 | 6.3 | 6.3 |
| 6 | Triethylhexanoin | | 4.0 | 4.0 | 4.0 | 4.0 |
| 7 | Neopentyl glycol dioctanoate | | 2.0 | 2.0 | 2.0 | 2.0 |
| 8 | Polymethylsilsesquioxane powder *5 | | 1.5 | 1.5 | 1.5 | 1.5 |
| 9 | 1,3-Butylene glycol | | 5.0 | 5.0 | 5.0 | 5.0 |
| 10 | Sodium chloride | | 0.5 | 0.5 | 0.5 | 0.5 |
| 11 | Water | | 50.0 | 50.0 | 50.0 | 50.0 |
| 12 | Silicone-treated titanium oxide *6 | | 8.65 | 8.65 | 8.65 | 8.65 |
| 13 | Silicone-treated red iron oxide *6 | | 0.45 | 0.45 | 0.45 | 0.45 |
| 14 | Silicone-treated yellow iron oxide *6 | | 0.75 | 0.75 | 0.75 | 0.75 |
| 15 | Silicone-treated black iron oxide *6 | | 0.15 | 0.15 | 0.15 | 0.15 |
| 16 | Silicone resin solution of Example 1 | | 5.0 | 5.0 | — | — |
| 17 | Silicone resin solution of Example 7 | | — | 5.0 | — | — |
| 18 | Silicone resin solution of Comparative Example 1 | | — | — | 5.0 | — |
| 19 | Silicone resin solution of Comparative Example 4 | | — | — | — | 5.0 |
| 20 | Antioxidant | | 0.5 | 0.5 | 0.5 | 0.5 |
| 21 | Preservative | | 1.0 | 1.0 | 1.0 | 1.0 |
| 22 | Perfume | | 0.2 | 0.2 | 0.2 | 0.2 |
| | Total | | 100 | 100 | 100 | 100 |

*1 KSG-210 by Shin-Etsu Chemical Co., Ltd.
*2 KSG-15 by Shin-Etsu Chemical Co., Ltd.
*3 KF-6017 by Shin-Etsu Chemical Co., Ltd.
*4 KF-96A-6cs by Shin-Etsu Chemical Co., Ltd.
*5 KMP-590 by Shin-Etsu Chemical Co., Ltd.
*6 treated with KF-9909 by Shin-Etsu Chemical Co., Ltd.

Preparation of Cosmetic Composition

An emulsion type cream foundation was prepared by stirring and mixing ingredients 1 to 4, part of 5, 6 to 8, 16 to 20, and 21 until uniform, dissolving ingredients 9 and 10 in ingredient 11 uniformly, moderately adding the solution to the mix, emulsifying the mixture, adding ingredients 12 to 15, remainder of 5, and 22 to the emulsion, mixing the contents, and filling a container therewith.

Evaluation of Feel on Use

A panel of fifty (50) professional female members evaluated the emulsion type cream foundation with respect to spread upon application, stickiness, color irregularity on finishing, lasting quality (retention, as evaluated after 8 hours from application). Ratings were assigned according to the criteria shown in Table 7. An average of ratings was calculated.

Secondary Transfer-Preventing Effect

The emulsion type cream foundation was coated to the forehead of panelists in a similar manner. After the lapse of 20 minutes from coating, tissue paper was pressed against the coated area. The effect of preventing any secondary transfer of the cosmetic composition was rated according to the criteria shown in Table 7. An average of ratings was calculated.

TABLE 7

| Point | Spread | Stickiness | Color irregularity | Lasting quality | Secondary transfer |
|---|---|---|---|---|---|
| 5 | excellent | nil | nil | excellent | nil |
| 4 | good | substantially nil | substantially nil | good | substantially nil |
| 3 | ordinary | ordinary | ordinary | ordinary | ordinary |
| 2 | rather poor | somewhat sticky | somewhat irregular | rather short | some |
| 1 | poor | sticky | noticeably irregular | opaque | noticeable |

Samples are marked based on the average of each evaluation item, with the results shown in Table 8.
◎: average≥4.0 points
○: 3.0 points≤average<4.0 points
Δ: 2.0 points≤average<3.0 points
X: average<2.0 points

TABLE 8

| | Example | | Comparative Example | |
|---|---|---|---|---|
| Item | 9 | 10 | 6 | 7 |
| Spread | ◎ | ○ | Δ | X |
| Stickiness | ◎ | ◎ | Δ | ○ |
| Color irregularity | ◎ | ◎ | ○ | Δ |
| Lasting quality | ◎ | ◎ | Δ | Δ |
| Secondary transfer | ◎ | ◎ | X | Δ |

As is evident from Table 8, the cosmetic compositions of the invention are improved in all evaluation items, especially in spread, lasting quality, and secondary transfer prevention over Comparative Examples.

Examples 11, 12 and Comparative Example 8

Evaluation of Feel on Use of Cosmetics

Using the silicone resin solution obtained in Example, a lipstick was prepared in accordance with the following formulation and preparation method. The lipstick was evaluated by the following tests.

TABLE 9

| | | Example | | Comparative Example |
|---|---|---|---|---|
| No. | Formulation (%) | 11 | 12 | 8 |
| 1 | Candelilla wax | 4.0 | 4.0 | 4.0 |
| 2 | Polyethylene | 2.0 | 2.0 | 2.0 |
| 3 | Microcrystalline wax | 3.0 | 3.0 | 3.0 |
| 4 | Ceresin | 7.0 | 7.0 | 7.0 |
| 5 | Stearyl-modified acrylic silicone resin *1 | 14.0 | 14.0 | 14.0 |

TABLE 9-continued

| | | Example | | Comparative Example |
|---|---|---|---|---|
| No. | Formulation (%) | 11 | 12 | 8 |
| 6 | Diphenyl dimethicone *2 | 17.8 | 17.8 | 17.8 |
| 7 | Silicone resin solution of Example 1 | 6.0 | — | — |
| 8 | Silicone resin solution of Example 7 | — | 6.0 | — |
| 9 | Silicone resin solution of Comparative Example 4 | — | — | 6.0 |
| 10 | Alkyl-modified branched polyglycerol-modified silicone *3 | 3.0 | 3.0 | 3.0 |
| 11 | Macadamia nut oil | 15.0 | 15.0 | 15.0 |
| 12 | Hydrogenated polyisobutene | 8.0 | 8.0 | 8.0 |
| 13 | Isotridecyl isononanoate | 5.0 | 5.0 | 5.0 |
| 14 | Perfume | 0.2 | 0.2 | 0.2 |
| 15 | Lipstick pigment | 10 | 10 | 10 |
| 16 | Mica | 5 | 5 | 5 |
| | Total | 100 | 100 | 100 |

*1 KP-561P by Shin-Etsu Chemical Co., Ltd.
*2 KF-54 by Shin-Etsu Chemical Co., Ltd.
*3 KF-6105 by Shin-Etsu Chemical Co., Ltd.

Preparation of Cosmetic Composition

A lipstick was prepared by step A of heating and mixing ingredients 1 to 12 until uniform, step B of adding ingredients 13 to 16 to A while heating, and mixing them until uniform, and step C of filling an air-tight container with B.

The lipstick thus obtained was found to be non-sticky, non-oily, non-blotting, and long lasting.

Evaluation of Feel on Use

A panel of 50 professional female members evaluated the lipstick with respect to spread upon application, stickiness, color irregularity upon finishing, lasting quality (retention, as evaluated after 8 hours from application) in accordance with the same method as used for the evaluation of the emulsion type cream foundation. The results are shown in Table 10.

TABLE 10

| | Example | | Comparative Example |
|---|---|---|---|
| Item | 11 | 12 | 8 |
| Spread | ◎ | ○ | Δ |
| Stickiness | ◎ | ◎ | ○ |
| Color irregularity | ◎ | ◎ | Δ |
| Lasting quality | ◎ | ◎ | Δ |

Exemplary formulations of cosmetic compositions are described below. They were evaluated for "spread" and "lasting quality" on the same criterion as above. The foundation was also evaluated for "secondary transfer-preventing effect" on the same criterion as above.

Example 13

| Powder foundation | | |
|---|---|---|
| | Formulation | Amount (%) |
| 1. | Silicone-treated titanium oxide *1 | 12.0 |
| 2. | Silicone-treated sericite *1 | 35.0 |
| 3. | Lecithin-treated talc | 35.1 |
| 4. | Lecithin-treated spherical nylon powder | 5.0 |
| 5. | Silicone-treated red iron oxide *1 | 0.4 |
| 6. | Silicone-treated yellow iron oxide *1 | 2.0 |
| 7. | Silicone-treated umber *1 | 0.4 |
| 8. | Silicone-treated black iron oxide *1 | 0.1 |
| 9. | Silicone resin solution of Example 1 | 3.0 |
| 10. | Crosslinked dimethylpolysiloxane *2 | 4.0 |
| 11. | Glyceryl trioctanoate | 1.5 |
| 12. | Silicone wax *3 | 1.5 |
| | Total | 100.0 |

*1 treated with KF-9909 by Shin-Etsu Chemical Co., Ltd.
*2 KSG-16 by Shin-Etsu Chemical Co., Ltd.
*3 KP-562P by Shin-Etsu Chemical Co., Ltd.

Preparation of Cosmetic Composition

A powder foundation was prepared by step A of grinding and mixing ingredients 1 to 8 until uniform, step B of mixing ingredients 9 to 12 until uniform, step C of adding B to A and mixing until uniform, and step D of press molding C in a mold.

The powder foundation thus obtained was light spreading and long lasting and free of secondary transfer.

Example 14

| Powder foundation | | |
|---|---|---|
| | Formulation | Amount (%) |
| 1. | Caprylylsilane-treated mica *1 | 40.0 |
| 2. | Silicone-treated talc *2 | 20.0 |
| 3. | Silicone-treated titanium oxide *2 | 8.0 |
| 4. | Silicone-treated microparticulate titanium oxide *2 | 5.0 |
| 5. | Silicone-treated barium sulfate *2 | 8.9 |
| 6. | Silicone-treated foundation pigment *2 | 7.0 |
| 7. | Phenyl-modified hybrid silicone composite powder *3 | 2.0 |
| 8. | Polymethylsilsesquioxane powder *4 | 0.4 |
| 9. | Preservative | 0.5 |
| 10. | Perfume | 0.2 |
| 11. | Silicone resin solution of Example 4 | 3.0 |
| 12. | Glyceryl trioctanoate | 3.0 |
| 13. | Squalane | 1.0 |
| 14. | Vaseline | 1.0 |
| | Total | 100.0 |

*1 treated with AES-3083 by Shin-Etsu Chemical Co., Ltd.
*2 treated with KF-9909 by Shin-Etsu Chemical Co., Ltd.
*3 KSP-300 by Shin-Etsu Chemical Co., Ltd.
*4 KMP-590 by Shin-Etsu Chemical Co., Ltd.

Preparation of Cosmetic Composition

A powder foundation was prepared by step A of grinding and mixing ingredients 1 to 9 until uniform, step B of mixing ingredients 11 to 14 until uniform, adding the mix to A and mixing until uniform, step C of adding ingredient 10 to B, and step D of press molding C in a mold.

The powder foundation thus obtained was light spreading and long lasting and free of secondary transfer.

Example 15

| Stick-type W/O foundation | | |
|---|---|---|
| | Formulation | Amount (%) |
| 1. | Ceresin | 5.5 |
| 2. | Inulin stearate | 2.0 |

Stick-type W/O foundation (continued)

| | Formulation | Amount (%) |
|---|---|---|
| 3. | Neopentyl glycol dioctanoate | 7.0 |
| 4. | Triethylhexanoin | 4.0 |
| 5. | Dimethylpolysiloxane (6cs) | 6.3 |
| 6. | Silicone resin solution of Example 2 | 3.0 |
| 7. | Crosslinked polyglycerol-modified silicone *1 | 4.0 |
| 8. | Alkyl-modified branched polyglycerol-modified silicone *2 | 1.5 |
| 9. | Polymethylsilsesquioxane powder *3 | 1.0 |
| 10. | Silicone-treated titanium oxide *4 | 9.0 |
| 11. | Silicone-treated foundation pigment *5 | 5.0 |
| 12. | Lecithin | 0.2 |
| 13. | Polysorbate 80 | 0.3 |
| 14. | 1,3-Butylene glycol | 4.0 |
| 15. | Preservative | 0.5 |
| 16. | Perfume | 0.2 |
| 17. | Purified water | 46.5 |
| | Total | 100.0 |

*1 KSG-710 by Shin-Etsu Chemical Co., Ltd.
*2 KF-6105 by Shin-Etsu Chemical Co., Ltd.
*3 KMP-590 by Shin-Etsu Chemical Co., Ltd.
*4 treated with KF-9909 by Shin-Etsu Chemical Co., Ltd.
*5 treated with KF-9909 by Shin-Etsu Chemical Co., Ltd.

Preparation of Cosmetic Composition

A stick-type W/O foundation was prepared by step A of heating and dissolving ingredients 1 to 9 until uniform, step B of mixing ingredients 10 to 13 and part of 14 and dispersing them on a roller, step C of uniformly dissolving remainder of 14, and ingredients 15 and 17, adding the solution to B, heating and dispersing the contents uniformly, step D of adding C to A while heating and stirring, emulsifying, and adding ingredient 16 to the emulsion, and step E of filling an air-tight container with D.

The stick-type W/O foundation thus obtained was light spreading and long lasting and free of secondary transfer.

Example 16

Solid in-oil polyhydric alcohol-emulsified blusher

| | Formulation | Amount (%) |
|---|---|---|
| 1. | Crosslinked polyglycerol-modified silicone *1 | 5.0 |
| 2. | Crosslinked dimethylpolysiloxane *2 | 5.0 |
| 3. | Decamethylcyclopentasiloxane | 3.0 |
| 4. | Dimethylpolysiloxane (6cs) | 19.7 |
| 5. | Cetyl isooctanoate | 5.0 |
| 6. | Silicone resin solution of Example 3 | 10.0 |
| 7. | Behenyl-modified acrylic silicone resin *3 | 3.0 |
| 8. | Paraffin wax (m.p. 80° C.) | 9.0 |
| 9. | Dimethyldistearylammonium hectorite | 0.3 |
| 10. | Acrylic silicone-treated powder *4 | 25.0 |
| 11. | Preservative | 0.5 |
| 12. | Perfume | 0.2 |
| 13. | 1,3-Butylene glycol | 14.3 |
| | Total | 100.0 |

*1 KSG-710 by Shin-Etsu Chemical Co., Ltd.
*2 KSG-15 by Shin-Etsu Chemical Co., Ltd.
*3 KP-562P by Shin-Etsu Chemical Co., Ltd.
*4 treated with KP-574 by Shin-Etsu Chemical Co., Ltd.

Preparation of Cosmetic Composition

A solid blusher was prepared by step A of mixing ingredients 1 to 9 and 12 until uniform while heating at 80° C., step B of adding ingredient 10 to A and dispersing the contents uniformly, step C of mixing ingredients 11 and 13 while heating at 80° C., adding the mix to B, and emulsifying, and step D of casting the emulsion into a metal tray and cooling.

The solid in-oil polyhydric alcohol-emulsified blusher thus obtained was light spreading, non-sticky and non-oily.

Example 17

Creamy lipstick

| | Formulation | Amount (%) |
|---|---|---|
| 1. | Palmitic acid/ethylhexanoic acid dextrin *1 | 9.0 |
| 2. | Triethylhexanoin | 7.0 |
| 3. | Silicone resin solution of Example 2 | 8.0 |
| 4. | Alkyl-modified crosslinked dimethylpolysiloxane *2 | 8.0 |
| 5. | Alkyl-modified branched polyglycerol-modified silicone *3 | 2.0 |
| 6. | Decamethylcyclopentasiloxane | 35.0 |
| 7. | 1,3-Butylene glycol | 4.8 |
| 8. | Purified water | 18.0 |
| 9. | Color pigment | 6.0 |
| 10. | Mica | 2.0 |
| 11. | Perfume | 0.2 |
| | Total | 100.0 |

*1 Rheopearl TT by Chiba Flour Milling Co., Ltd.
*2 KSG-43 by Shin-Etsu Chemical Co., Ltd.
*3 KF-6105 by Shin-Etsu Chemical Co., Ltd.

Preparation of Cosmetic Composition

A creamy lipstick was prepared by step A of mixing ingredient 1, part of 2, ingredients 3 to 6 until uniform while heating, step B of mixing remainder of 2 with ingredient 9, dispersing the mix on a roller, adding the dispersion to A, and mixing the contents uniformly, step C of mixing ingredients 7 and 8 while heating, adding the mix to B, and emulsifying, and step D of adding ingredients 10 and 11 to C.

The creamy lipstick thus obtained was light spreading, easy to spread on the lip, non-sticky, non-oily, and long lasting.

Example 18

Eye liner

| | Formulation | Amount (%) |
|---|---|---|
| 1. | Tristrimethylsiloxymethylsilane *1 | 20.0 |
| 2. | Polyether-modified silicone *2 | 3.0 |
| 3. | Silicone resin solution of Example 2 | 33.5 |
| 4. | Silicone reticulate resin liquid *3 | 15.0 |
| 5. | Dimethyldistearylammonium hectorite | 3.0 |
| 6. | Silicone-treated black iron oxide *4 | 10.0 |
| 7. | 1,3-Butylene glycol | 4.5 |
| 8. | Sodium sulfate | 0.5 |
| 9. | Preservative | 0.5 |
| 10. | Purified water | 10.0 |
| | Total | 100.0 |

*1 TMF-1.5 by Shin-Etsu Chemical Co., Ltd.
*2 KF-6017 by Shin-Etsu Chemical Co., Ltd.
*3 KF-7312T by Shin-Etsu Chemical Co., Ltd.
*4 treated with KF-9901 by Shin-Etsu Chemical Co., Ltd.

Preparation of Cosmetic Composition

An eye liner was prepared by step A of mixing ingredients 1 to 5, adding ingredient 6 thereto, mixing and dispersing the contents uniformly, step B of mixing ingredients 7 to 10, step C of adding B to A and emulsifying the contents.

The eye liner thus obtained was light spreading, easy to draw eye lines, light feeling, and very long lasting.

Example 19

| | Mascara | |
|---|---|---|
| | Formulation | Amount (%) |
| 1. | Silicone resin solution of Example 1 | 26.5 |
| 2. | Palmitic acid/ethylhexanoic acid dextrin *1 | 3.0 |
| 3. | Ceresin | 2.5 |
| 4. | Behenyl-modified acrylic silicone resin *2 | 2.0 |
| 5. | Beeswax | 3.5 |
| 6. | Triethylhexanoin | 3.0 |
| 7. | Dimethyldistearylammonium hectorite | 4.0 |
| 8. | Lecithin | 0.5 |
| 9. | Isododecane | 34.0 |
| 10. | Silicone-treated pigment *3 | 5.0 |
| 11. | Silica | 3.0 |
| 12. | Talc | 12.0 |
| 13. | Branched polyether-modified silicone *4 | 1.0 |
| | Total | 100.0 |

*1 Rheopearl TT by Chiba Flour Milling Co., Ltd.
*2 KP-562P by Shin-Etsu Chemical Co., Ltd.
*3 treated with KF-9909 by Shin-Etsu Chemical Co., Ltd.
*4 KF-6028P by Shin-Etsu Chemical Co., Ltd.

Preparation of Cosmetic Composition

A mascara was prepared by step A of adding ingredients 7 and 13 to ingredient 9 and mixing the contents uniformly while heating, step B of adding ingredients 1 to 6 and 8 to A and mixing the contents uniformly, step C of adding ingredients 10, 11 and 12 to B, and uniformly dispersing the contents on a roller.

The mascara thus obtained was light spreading, easy to adhere to eyelashes, non-sticky feeling, and very long lasting.

Example 20

| | Creamy eye shadow | |
|---|---|---|
| | Formulation | Amount (%) |
| 1. | Decamethylcyclopentasiloxane | 15.0 |
| 2. | Dimethylpolysiloxane (6cs) | 4.0 |
| 3. | Silicone resin solution of Example 3 | 5.0 |
| 4. | Branched polyether-modified silicone *1 | 1.5 |
| 5. | Acrylic silicone resin-treated pigment *2 | 16.0 |
| 6. | Sodium chloride | 2.0 |
| 7. | Propylene glycol | 7.5 |
| 8. | Preservative | 0.5 |
| 9. | Purified water | 48.5 |
| | Total | 100.0 |

*1 KF-6028P by Shin-Etsu Chemical Co., Ltd.
*2 treated with KP-574 by Shin-Etsu Chemical Co., Ltd.

Preparation of Cosmetic Composition

A creamy eye shadow was prepared by step A of mixing ingredients 1 to 4, adding ingredient 5 thereto and mixing and dispersing the contents uniformly, step B of mixing ingredients 6 to 9, step C of adding B to A, and emulsifying the contents.

The creamy eye shadow thus obtained was light spreading, non-oily, powdery texture-free, and long lasting.

Example 21

| | Creamy eye shadow | |
|---|---|---|
| | Formulation | Amount (%) |
| 1. | Acrylic silicone resin liquid *1 | 3.0 |
| 2. | Stearyl-modified acrylic silicone resin *2 | 2.0 |
| 3. | Branched polyether-modified silicone *3 | 1.5 |
| 4. | Decamethylcyclopentasiloxane | 20.3 |
| 5. | Silicone resin solution of Example 4 | 10.0 |
| 6. | Dimethyldistearylammonium hectorite | 1.2 |
| 7. | Acrylic silicone resin-treated pigment *4 | 20.0 |
| 8. | Spherical nylon | 3.0 |
| 9. | Talc | 4.0 |
| 10. | Ethanol | 5.0 |
| 11. | Purified water | 30.0 |
| | Total | 100.0 |

*1 KP-545 by Shin-Etsu Chemical Co., Ltd.
*2 KP-561P by Shin-Etsu Chemical Co., Ltd.
*3 KF-6028P by Shin-Etsu Chemical Co., Ltd.
*4 treated with KP-574 by Shin-Etsu Chemical Co., Ltd.

Preparation of Cosmetic Composition

A creamy eye shadow was prepared by step A of mixing ingredients 1 to 6, adding ingredients 7 to 9 thereto and mixing and dispersing the contents uniformly, step B of mixing ingredients 10 and 11, step C of adding B to A and emulsifying the contents.

The creamy eye shadow thus obtained was light spreading, non-oily, powdery texture-free, fresh looking, and long lasting.

Example 22

| | Sun cutting milky lotion | |
|---|---|---|
| | Formulation | Amount (%) |
| 1. | Crosslinked polyether-modified silicone *1 | 3.0 |
| 2. | Crosslinked dimethylpolysiloxane *2 | 2.0 |
| 3. | Branched polyether-modified silicone *3 | 1.0 |
| 4. | Silicone resin solution of Example 1 | 5.0 |
| 5. | Decamethylcyclopentasiloxane | 5.0 |
| 6. | Isotridecyl isononanoate | 4.0 |
| 7. | Titanium oxide dispersion *4 | 25.0 |
| 8. | Zinc oxide dispersion *5 | 35.0 |
| 9. | 1,3-Butylene glycol | 2.0 |
| 10. | Sodium citrate | 0.2 |
| 11. | Sodium chloride | 0.5 |
| 12. | Purified water | 17.3 |
| | Total | 100.0 |

*1 KSG-210 by Shin-Etsu Chemical Co., Ltd.
*2 KSG-15 by Shin-Etsu Chemical Co., Ltd.
*3 KF-6028P by Shin-Etsu Chemical Co., Ltd.
*4 SPD-T5 by Shin-Etsu Chemical Co., Ltd.
*5 SPD-Z5 by Shin-Etsu Chemical Co., Ltd.

Preparation of Cosmetic Composition

A sun cutting milky lotion was prepared by step A of mixing ingredients 1 to 6 until uniform, step B of mixing ingredients 9 to 12, step C of adding B to A, emulsifying and adding ingredients 7 and 8 thereto.

The sun cutting milky lotion thus obtained was light spreading, non-sticky, non-oily, and antiperspirant.

Example 23

| | Sun cutting cream | |
|---|---|---|
| | Formulation | Amount (%) |
| 1. | Crosslinked polyether-modified silicone *1 | 3.0 |
| 2. | Crosslinked dimethylpolysiloxane *2 | 2.0 |
| 3. | Alkyl-modified branched polyether-modified silicone *3 | 1.0 |
| 4. | Silicone resin solution of Example 3 | 7.0 |
| 5. | Decamethylcyclopentasiloxane | 15.5 |
| 6. | Octyl p-methoxycinnamate | 6.0 |
| 7. | Acrylic silicone resin liquid *4 | 10.0 |
| 8. | Lipophilic treated microparticulate zinc oxide *5 | 20.0 |
| 9. | 1,3-Butylene glycol | 1.8 |
| 10. | Sodium citrate | 0.2 |
| 11. | Sodium chloride | 0.5 |
| 12. | Perfume | 0.2 |
| 13. | Purified water | 32.8 |
| | Total | 100.0 |

*1 KSG-240 by Shin-Etsu Chemical Co., Ltd.
*2 KSG-15 by Shin-Etsu Chemical Co., Ltd.
*3 KF-6038 by Shin-Etsu Chemical Co., Ltd.
*4 KP-575 by Shin-Etsu Chemical Co., Ltd.
*5 treated with AES-3083 by Shin-Etsu Chemical Co., Ltd.

Preparation of Cosmetic Composition

A sun cutting cream was prepared by step A of adding ingredient 7 to part of ingredient 5, mixing uniformly, adding ingredient 8 thereto, dispersing the contents on a bead mill, step B of mixing ingredients 1 to 4, remainder of 5, and 6 until uniform, step C of mixing ingredients 9 to 11, and 13 until uniform, and step D of adding C to B, emulsifying, and adding A and ingredient 12 thereto.

The sun cutting cream thus obtained was light spreading, non-sticky, non-oily, light feeling, and long lasting.

Example 24

| | Sun cutting lotion (shaking type) | |
|---|---|---|
| | Formulation | Amount (%) |
| 1. | Branched polyether-modified silicone *1 | 2.0 |
| 2. | Silicone resin solution of Example 2 | 5.0 |
| 3. | Dimethylpolysiloxane (6cs) | 3.0 |
| 4. | Decamethylcyclopentasiloxane | 7.8 |
| 5. | Octyl p-methoxycinnamate | 7.5 |
| 6. | Hybrid silicone composite powder *2 | 0.5 |
| 7. | Dimethyldistearylammonium hectorite | 0.2 |
| 8. | Zinc oxide dispersion *3 | 45.0 |
| 9. | 1,3-Butylene glycol | 3.0 |
| 10. | Alcohol | 5.0 |
| 11. | Sodium citrate | 0.2 |
| 12. | Sodium chloride | 0.5 |
| 13. | Purified water | 20.3 |
| | Total | 100.0 |

*1 KF-6028P by Shin-Etsu Chemical Co., Ltd.
*2 KSP-105 by Shin-Etsu Chemical Co., Ltd.
*3 SPD-Z6 by Shin-Etsu Chemical Co., Ltd.

Preparation of Cosmetic Composition

A sun cutting lotion of shaking type was prepared by step A of mixing ingredients 1 to 7 until uniform, step B of mixing ingredients 9 to 13 until uniform, step C of adding B to A and emulsifying the contents, and step D of adding ingredient 8 thereto.

The sun cutting lotion thus obtained was light spreading, non-sticky, non-oily, and very long lasting.

Example 25

| | Suntan milky lotion | |
|---|---|---|
| | Formulation | Amount (%) |
| 1. | Crosslinked polyether-modified silicone *1 | 2.0 |
| 2. | Crosslinked dimethylpolysiloxane *2 | 3.0 |
| 3. | Polyether-modified silicone *3 | 1.5 |
| 4. | Silicone resin solution of Example 1 | 2.0 |
| 5. | Dimethylpolysiloxane (6cs) | 10.0 |
| 6. | Decamethylcyclopentasiloxane | 15.3 |
| 7. | Dihydroxyacetone | 2.0 |
| 8. | Glycerol | 10.0 |
| 9. | 1,3-Butylene glycol | 5.0 |
| 10. | Sodium citrate | 0.2 |
| 11. | Sodium chloride | 0.5 |
| 12. | Antioxidant | 0.5 |
| 13. | Preservative | 0.5 |
| 14. | Perfume | 0.2 |
| 15. | Purified water | 47.3 |
| | Total | 100.0 |

*1 KSG-210 by Shin-Etsu Chemical Co., Ltd.
*2 KSG-15 by Shin-Etsu Chemical Co., Ltd.
*3 KF-6017 by Shin-Etsu Chemical Co., Ltd.

Preparation of Cosmetic Composition

A suntan milky lotion was prepared by step A of mixing ingredients 1 to 6 until uniform, step B of mixing ingredients 7 to 13, and 15, step C of adding B to A, emulsifying, and adding ingredient 14 thereto.

The suntan milky lotion thus obtained was light spreading, non-sticky, and non-oily, and gave a light feeling.

Example 26

| | Suntan cream | |
|---|---|---|
| | Formulation | Amount (%) |
| 1. | Alkyl-modified crosslinked polyether-modified silicone *1 | 4.0 |
| 2. | Alkyl-modified crosslinked dimethylpolysiloxane *2 | 2.0 |
| 3. | Alkyl-modified branched polyether-modified silicone *3 | 1.0 |
| 4. | Silicone resin solution of Example 3 | 5.0 |
| 5. | Decamethylcyclopentasiloxane | 10.3 |
| 6. | Stearyl-modified acrylic silicone *4 | 1.0 |
| 7. | Dimethyloctyl p-aminobenzoate | 1.5 |
| 8. | 4-t-butyl-4'-methoxydibenzoylmethane | 1.5 |
| 9. | Kaolin | 0.5 |
| 10. | Pigment | 8.0 |
| 11. | Titanium oxide-coated mica | 8.0 |
| 12. | Dioctadecyldimethylammonium chloride | 0.1 |
| 13. | Sodium L-glutamate | 3.0 |
| 14. | 1,3-Butylene glycol | 4.0 |
| 15. | Sodium citrate | 0.2 |
| 16. | Sodium chloride | 0.5 |
| 17. | Antioxidant | 0.5 |
| 18. | Preservative | 0.5 |
| 19. | Perfume | 0.2 |
| 20. | Purified water | 48.2 |
| | Total | 100.0 |

*1 KSG-320 by Shin-Etsu Chemical Co., Ltd.
*2 KSG-42 by Shin-Etsu Chemical Co., Ltd.
*3 KF-6038 by Shin-Etsu Chemical Co., Ltd.
*4 KP-561P by Shin-Etsu Chemical Co., Ltd.

Preparation of Cosmetic Composition

A suntan cream was prepared by step A of heating and mixing ingredients 1 to 8, 17 and 18, step B of heating and stirring ingredient 12 and part of 20, adding ingredients 9 to 11 thereto, and dispersing the contents, step C of dissolving ingredients 13 to 16 and remainder of 20 uniformly and mixing the solution with B, and step D of slowly adding C to A while stirring, emulsifying, cooling, and adding ingredient 19 thereto.

The suntan cream thus obtained was fine textured, light spreading, non-sticky, non-oily, and long lasting, and gave a light feeling.

Example 27

Liquid W/O foundation

| | Formulation | Amount (%) |
|---|---|---|
| 1. | Decamethylcyclopentasiloxane | 18.0 |
| 2. | Dimethylpolysiloxane (6cs) | 2.0 |
| 3. | Silicone resin solution of Example 1 | 7.0 |
| 4. | Alkyl-modified branched polyether-modified silicone *1 | 2.0 |
| 5. | Octyl p-methoxycinnamate | 3.0 |
| 6. | Fluorine-modified silicone *2 | 2.0 |
| 7. | Polymethylsilsesquioxane powder *3 | 1.5 |
| 8. | Fluorine compound-treated foundation pigment *4 | 9.3 |
| 9. | Fluorine compound-treated mica titanium *4 | 2.0 |
| 10. | Silicone-treated microcrystalline titanium oxide *5 | 8.0 |
| 11. | Alkyl-modified branched polyglycerol-modified silicone *6 | 1.2 |
| 12. | Ethanol | 3.0 |
| 13. | 1,3-Butylene glycol | 4.3 |
| 14. | Glycerol | 1.5 |
| 15. | Magnesium sulfate | 0.5 |
| 16. | Antioxidant | 0.5 |
| 17. | Preservative | 0.5 |
| 18. | Perfume | 0.2 |
| 19. | Purified water | 33.5 |
| | Total | 100.0 |

*1 KF-6038 by Shin-Etsu Chemical Co., Ltd.
*2 FL-5 by Shin-Etsu Chemical Co., Ltd.
*3 KMP-590 by Shin-Etsu Chemical Co., Ltd.
*4 coated with 5% of diethanolamine salt of perfluoroalkylethyl phosphate
*5 treated with KF-9909 by Shin-Etsu Chemical Co., Ltd.
*6 KF-6105 by Shin-Etsu Chemical Co., Ltd.

Preparation of Cosmetic Composition

A liquid W/O foundation was prepared by step A of mixing part of ingredient 1, ingredients 11 and 12, and part of ingredient 20 and dispersing them uniformly, step B of mixing ingredients 8 to 10 until uniform, step C of mixing remainder of ingredient 1, ingredients 2 to 7, adding B thereto, dispersing and mixing the contents uniformly, step D of mixing ingredients 13 to 18 and remainder of 20 until uniform, and step E of slowly adding ID to C while stirring, emulsifying, and adding A and ingredient 19 thereto.

The liquid W/O foundation thus obtained was non-sticky, light feeling, light spreading, non-oily, long lasting, and free of secondary transfer.

Example 28

Hair cream

| | Formulation | Amount (%) |
|---|---|---|
| 1. | Decamethylcyclopentasiloxane | 16.0 |
| 2. | Methylphenylpolysiloxane *1 | 2.0 |
| 3. | Silicone resin solution of Example 1 | 4.0 |
| 4. | Squalane | 5.0 |
| 5. | Silicone reticulate resin liquid *2 | 2.0 |
| 6. | Sorbitan sesquiisostearate | 1.5 |
| 7. | Alkyl-modified branched polyether-modified silicone *3 | 2.0 |
| 8. | Sodium sorbitol sulfate | 2.0 |
| 9. | Sodium chondroitin sulfate | 1.0 |
| 10. | Sodium hyaluronate | 0.5 |
| 11. | Propylene glycol | 2.3 |
| 12. | Presevative | 1.5 |
| 13. | Vitamin E acetate | 0.1 |
| 14. | Antioxidant | 0.5 |
| 15. | Perfume | 0.2 |
| 16. | Purified water | 59.4 |
| | Total | 100.0 |

*1 KF-54 by Shin-Etsu Chemical Co., Ltd.
*2 KF-7312J by Shin-Etsu Chemical Co., Ltd.
*3 KF-6038 by Shin-Etsu Chemical Co., Ltd.

Preparation of Cosmetic Composition

A hair cream was prepared by step A of mixing ingredients 1 to 7 and 12 to 14 until uniform, step B of mixing ingredients 8 to 11 and 16 until uniform, step C of slowly adding B to A while stirring, emulsifying, and adding ingredient 15 thereto.

The hair cream thus obtained was non-oily, light spreading, water resistant, water repellent, antiperspirant, and long lasting.

Example 29

Hair cream

| | Formulation | Amount (%) |
|---|---|---|
| 1. | Silicone gum liquid *1 | 10.0 |
| 2. | Silicone reticulate resin liquid *2 | 10.0 |
| 3. | Silicone resin solution of Example 3 | 10.0 |
| 4. | Glyceryl tri-2-ethylhexanoate | 5.0 |
| 5. | Vaseline | 5.0 |
| 6. | Stearic acid | 1.5 |
| 7. | Cetyl alcohol | 0.5 |
| 8. | Polyglyceryl monooleate | 1.5 |
| 9. | Glyceryl monostearate | 1.5 |
| 10. | Polyether-modified silicone *3 | 0.5 |
| 11. | 1,3-Butylene glycol | 5.0 |
| 12. | Acrylate/C10-C30 alkyl acrylate cross-polymer *4 | 0.3 |
| 13. | Triethanolamine | 0.3 |
| 14. | Preservative | 0.5 |
| 15. | Perfume | 0.2 |
| 16. | Purified water | 48.2 |
| | Total | 100.0 |

*1 KF-9028 by Shin-Etsu Chemical Co., Ltd.
*2 KF-7312J by Shin-Etsu Chemical Co., Ltd.
*3 KF-6011 by Shin-Etsu Chemical Co., Ltd.
*4 Pemulen TR-1 by Lubrizol Advanced Materials Corp.

Preparation of Cosmetic Composition

A hair cream was prepared by step A of heating and dissolving ingredients 1 to 10 and 14, step B of mixing ingredients 11 to 13 and 16 while heating, step C of slowly adding A to B while stirring, emulsifying, cooling, and adding ingredient 15 thereto.

The hair cream thus obtained was light spreading, gave luster and smoothness to the hair, and had an excellent hair setting effect, water resistance, antiperspirant action, and long lasting quality.

Example 30

Humectant O/W cream

| | Formulation | Amount (%) |
|---|---|---|
| 1. | Silicone resin solution of Example 1 | 4.0 |
| 2. | Liquid paraffin | 4.5 |
| 3. | Macadamia nut oil | 5.0 |
| 4. | Dimethylpolysiloxane (viscosity 6 mm2/s @ 25° C.) | 5.0 |
| 5. | Octyl p-methoxycinnamate | 5.0 |
| 6. | Alkyl-modified branched polyglycerol-modified silicone *1 | 1.5 |
| 7. | Propylene glycol | 8.0 |
| 8. | Glycerol | 3.0 |
| 9. | Preservative | 0.5 |
| 10. | Perfume | 0.2 |
| 11. | Purified water | 63.3 |
| | Total | 100.0 |

*1 KF-6105 by Shin-Etsu Chemical Co., Ltd.

Preparation of Cosmetic Composition

A humectant O/W cream was prepared by step A of mixing ingredients 1 to 6 until uniform, and step B of mixing ingredients 7 to 11, adding the mixture to A and emulsifying.

The humectant O/W cream thus obtained was light spreading, gave a light feeling, and sustained a humectant effect.

Example 31

Emollient O/W cream

| | Formulation | Amount (%) |
|---|---|---|
| 1. | Crosslinked dimethylpolysiloxane *1 | 7.0 |
| 2. | Crosslinked dimethylpolysiloxane *2 | 30.0 |
| 3. | Silicone resin solution of Example 2 | 6.0 |
| 4. | Decamethylcyclopentasiloxane | 5.0 |
| 5. | 1,3-Butylene glycol | 4.0 |
| 6. | Branched polyglycerol-modified silicone *3 | 0.6 |
| 7. | Branched polyglycerol-modified silicone *4 | 0.3 |
| 8. | Acrylamide/acryloyldimethyltaurine Na copolymer *5 | 0.6 |
| 9. | Dimethyltaurineammonium acrylate/VP copolymer *6 | 0.7 |
| 10. | Sodium chloride | 0.1 |
| 11. | Purified water | 45.7 |
| | Total | 100.0 |

*1 KSG-15 by Shin-Etsu Chemical Co., Ltd.
*2 KSG-16 by Shin-Etsu Chemical Co., Ltd.
*3 KF-6104 by Shin-Etsu Chemical Co., Ltd.
*4 KF-6100 by Shin-Etsu Chemical Co., Ltd.
*5 Simulgel 600 by Seppic
*6 Aristoflex AVC by Clariant Preparation of Cosmetic Composition An emollient O/W cream was prepared by step A of mixing ingredients 1 to 4 until uniform, step B of mixing ingredients 5 to 11 until uniform, and step C of slowly adding A to B while stirring, and mixing.

The emollient O/W cream thus obtained was non-oily, light feeling, and light spreading and sustained a skin protecting effect.

Example 32

Hand cream

| | Formulation | Amount (%) |
|---|---|---|
| 1. | Decamethylcyclopentasiloxane | 25.0 |
| 2. | Silicone resin solution of Example 4 | 10.0 |
| 3. | Liquid paraffin | 5.0 |
| 4. | Amino-modified silicone gum liquid *1 | 8.0 |
| 5. | Branched polyether-modified silicone *2 | 2.0 |
| 6. | Hybrid silicone composite powder *3 | 2.5 |
| 7. | Distearyldimethylammonium chloride | 0.8 |
| 8. | Vitamin E acetate | 0.1 |
| 9. | Polyethylene glycol 400 | 1.0 |
| 10. | Glycerol | 10.0 |
| 11. | Aluminum magnesium silicate | 1.2 |
| 12. | Preservative | 0.5 |
| 13. | Perfume | 0.2 |
| 14. | Purified water | 33.7 |
| | Total | 100.0 |

*1 KF-8108 by Shin-Etsu Chemical Co., Ltd.
*2 KF-6028P by Shin-Etsu Chemical Co., Ltd.
*3 KSP-102 by Shin-Etsu Chemical Co., Ltd.

Preparation of Cosmetic Composition

A hand cream was prepared by step A of mixing ingredients 1 to 8 and 12 until uniform, step B of mixing ingredients 9 to 11 and 14 until uniform, and step C of slowly adding B to A while stirring, emulsifying, and adding ingredient 13 thereto.

The hand cream thus obtained was non-oily, light feeling, and light spreading and sustained a skin protecting effect.

Example 33

O/W cream

| | Formulation | Amount (%) |
|---|---|---|
| 1. | Dimethylpolysiloxane (6cs) | 7.0 |
| 2. | Stearyl-modified acrylic silicone resin *1 | 8.0 |
| 3. | Silicone resin solution of Example 3 | 5.0 |
| 4. | Glyceryl triisostearate | 10.0 |
| 5. | Cetanol | 1.0 |
| 6. | Stearic acid | 3.0 |
| 7. | Glyceryl monostearate | 1.5 |
| 8. | Sorbitan sesquioleate | 0.5 |
| 9. | Polyoxyethylene sorbitan monooleate | 1.0 |
| 10. | Sodium hydroxide (1% aqueous solution) | 10.0 |
| 11. | 1,3-Butylene glycol | 5.0 |
| 12. | Preservative | 0.5 |
| 13. | Perfume | 0.2 |
| 14. | Purified water | 54.8 |
| | Total | 100.0 |

*1 KP-561P by Shin-Etsu Chemical Co., Ltd.

Preparation of Cosmetic Composition

An O/W cream was prepared by step A of mixing ingredients 1 to 9 while heating, step B of mixing ingredients 10 to 12 and 14 while heating, and step C of slowly adding B to A while stirring, cooling and adding ingredient 13 thereto.

The O/W cream thus obtained was non-sticky, non-oily, and light spreading, and gave a light dry feeling.

Example 34

| O/W cream | | |
|---|---|---|
| | Formulation | Amount (%) |
| 1. | Polyglyceryl monooleate | 1.0 |
| 2. | Cetyl alcohol | 0.5 |
| 3. | Stearic acid | 1.0 |
| 4. | Glyceryl monostearate | 1.0 |
| 5. | Silicone resin solution of Example 1 | 2.0 |
| 6. | Macadamia nut oil | 9.0 |
| 7. | Crosslinked dimethylpolysiloxane *1 | 0.5 |
| 8. | Acrylate/C10-C30 alkyl acrylate cross-polymer *2 | 0.2 |
| 9. | Methyl cellulose | 0.1 |
| 10. | Triethanolamine | 0.2 |
| 11. | 1,3-Butylene glycol | 7.0 |
| 12. | Preservative | 0.5 |
| 13. | Perfume | 0.2 |
| 14. | Purified water | 76.8 |
| | Total | 100.0 |

*1 KSG-16 by Shin-Etsu Chemical Co., Ltd.
*2 Pemulen TR-1 by Lubrizol Advanced Materials Corp.

Preparation of Cosmetic Composition

An O/W cream was prepared by step A of heating and mixing ingredients 1 to 7 until uniform, step B of mixing ingredients 8 to 12 and 14 while heating, and step C of slowly adding B to A while stirring, emulsifying, cooling and adding ingredient 13 thereto.

The O/W cream thus obtained was non-sticky, non-oily, and light spreading, gave a dry feeling, and maintained a skin freshlooking effect.

Example 35

| Antiperspirant | | |
|---|---|---|
| | Formulation | Amount (%) |
| 1. | Crosslinked polyether-modified silicone *1 | 7.0 |
| 2. | Silicone resin solution of Example 2 | 8.0 |
| 3. | Decamethylcyclopentasiloxane | 9.0 |
| 4. | 1,3-Butylene glycol | 5.0 |
| 5. | Sodium citrate | 0.2 |
| 6. | Glycine salt of aluminum zirconium tetrachloride hydrate | 20.0 |
| 7. | Purified water | 50.8 |
| | Total | 100.0 |

*1 KSG-210 by Shin-Etsu Chemical Co., Ltd.

Preparation of Cosmetic Composition

An antiperspirant was prepared by step A of mixing ingredients 1 to 3 until uniform, step B of mixing ingredients 4 to 7 until uniform, and step C of slowly adding B to A while stirring, and emulsifying.

The antiperspirant thus obtained was light spreading, caused no white-staining to the skin, and sustained an antiperspirant effect.

Example 36

| Wrinkle concealer | | |
|---|---|---|
| | Formulation | Amount (%) |
| 1. | Crosslinked polyether-modified silicone *1 | 5.0 |
| 2. | Crosslinked dimethylpolysiloxane *2 | 55.0 |
| 3. | Silicone resin solution of Example 1 | 15.0 |
| 4. | Decamethylcyclopentasiloxane | 8.0 |
| 5. | Hybrid silicone composite powder *3 | 12.0 |
| 6. | Silicone gum liquid *4 | 5.0 |
| | Total | 100.0 |

*1 KSG-210 by Shin-Etsu Chemical Co., Ltd.
*2 KSG-15 by Shin-Etsu Chemical Co., Ltd.
*3 KSP-101 by Shin-Etsu Chemical Co., Ltd.
*4 KF-9028 by Shin-Etsu Chemical Co., Ltd.

Preparation of Cosmetic Composition

A wrinkle concealer was prepared by step A of mixing ingredients 1 to 6 until uniform.

The wrinkle concealer thus obtained was non-sticky, non-oily, and light spreading, gave a dry feeling, and sustained a sealing effect.

Example 37

| Cleansing cream | | |
|---|---|---|
| | Formulation | Amount (%) |
| 1. | Dimethylpolysiloxane (6cs) | 5.0 |
| 2. | Methylphenylpolysiloxane *1 | 5.0 |
| 3. | Liquid paraffin | 5.0 |
| 4. | Jojoba oil | 2.0 |
| 5. | Silicone resin solution of Example 4 | 4.0 |
| 6. | Branched polyether-modified silicone *2 | 2.0 |
| 7. | Dextrin fatty acid ester | 0.8 |
| 8. | Aluminum monostearate | 0.2 |
| 9. | Aluminum chloride | 1.0 |
| 10. | Glycerol | 10.0 |
| 11. | Preservative | 0.5 |
| 12. | Perfume | 0.2 |
| 13. | Purified water | 64.3 |
| | Total | 100.0 |

*1 KF-56 by Shin-Etsu Chemical Co., Ltd.
*2 KF-6028 by Shin-Etsu Chemical Co., Ltd.

Preparation of Cosmetic Composition

A cleansing cream was prepared by step A of mixing ingredients 1 to 8 while heating, step B of mixing ingredients 9 to 11 and 13 while heating, and step C of slowly adding B to A while stirring, emulsifying, cooling, adding ingredient 12 thereto.

The cleansing cream thus obtained was light spreading and gave a moist, fresh, dry feeling.

Example 38

| Transparent cleansing lotion | | |
|---|---|---|
| | Formulation | Amount (%) |
| 1. | Decamethylcyclopentasiloxane | 50.8 |
| 2. | Silicone resin solution of Example 1 | 5.0 |
| 3. | Neopentylglycol dioctanoate | 6.0 |

-continued

| Transparent cleansing lotion | | |
|---|---|---|
| | Formulation | Amount (%) |
| 4. | Silica | 0.2 |
| 5. | 1,3-Butylene glycol | 5.0 |
| 6. | Glycerol | 6.0 |
| 7. | Polyether-modified silicone *1 | 5.0 |
| 8. | Polyether-modified silicone *2 | 3.0 |
| 9. | PEG-60 hydrogenated castor oil | 2.0 |
| 10. | Purified water | 17.0 |
| | Total | 100.0 |

*1 KF-6011 by Shin-Etsu Chemical Co., Ltd.
*2 KF-6013 by Shin-Etsu Chemical Co., Ltd.

Preparation of Cosmetic Composition

A transparent cleansing lotion was prepared by step A of mixing ingredients 1 to 4 until uniform, step B of mixing ingredients 5 to 10 until uniform, and step C of slowly adding A to B while stirring, and emulsifying.

The cleansing lotion thus obtained was light spreading, gave a moist fresh feeling and exerted a satisfactory cleansing effect.

Example 39

| W/O blusher | | |
|---|---|---|
| | Formulation | Amount (%) |
| 1. | Acrylic silicone resin liquid *1 | 10.0 |
| 2. | Stearyl-modified acrylic silicone resin *2 | 2.0 |
| 3. | Branched polyether-modified silicone *3 | 1.5 |
| 4. | Decamethylcyclopentasiloxane | 15.0 |
| 5. | Glyceryl triisostearate | 3.0 |
| 6. | Silicone resin solution of Example 2 | 5.0 |
| 7. | Dimethyldistearylammonium hectorite | 1.5 |
| 8. | Spherical nylon | 3.0 |
| 9. | Talc | 4.0 |
| 10. | Blusher pigment (treated with acrylic silicone) *4 | 20.0 |
| 11. | Alcohol | 5.0 |
| 12. | Perfume | 0.2 |
| 13. | Purified water | 29.8 |
| | Total | 100.0 |

*1 KP-545 by Shin-Etsu Chemical Co., Ltd.
*2 KP-561P by Shin-Etsu Chemical Co., Ltd.
*3 KF-6028P by Shin-Etsu Chemical Co., Ltd.
*4 treated with KP-574 by Shin-Etsu Chemical Co., Ltd.

Preparation of Cosmetic Composition

A W/O blusher was prepared by step A of mixing ingredients 1 to 7 while heating, step B of mixing ingredients 8 to 10 and 12 until uniform, step C of mixing A and B, step D of mixing ingredients 11 and 13, and step E of slowly adding D to C while stirring, and emulsifying.

The W/O blusher thus obtained was non-sticky, non-oily, light spreading, adherent, and long lasting.

Example 40

| W/O liquid foundation | | |
|---|---|---|
| | Formulation | Amount (%) |
| 1. | Crosslinked polyether-modified silicone *1 | 3.0 |
| 2. | Crosslinked dimethylpolysiloxane *2 | 5.0 |

-continued

| W/O liquid foundation | | |
|---|---|---|
| | Formulation | Amount (%) |
| 3. | Branched polyether-modified silicone *3 | 2.0 |
| 4. | Decamethylcyclopentasiloxane | 20.0 |
| 5. | Cetyl isooctanoate | 5.0 |
| 6. | Silicone resin solution of Example 2 | 10.0 |
| 7. | Dimethyldistearylammonium hectorite | 1.2 |
| 8. | Foundation pigment (silicone-treated) *4 | 14.0 |
| 9. | Acrylic silicone resin liquid *5 | 10.0 |
| 10. | 1,3-Butylene glycol | 5.0 |
| 11. | Xanthan gum | 0.1 |
| 12. | Sodium citrate | 0.2 |
| 13. | Sodium chloride | 0.5 |
| 14. | Preservative | 0.5 |
| 15. | Perfume | 0.2 |
| 16. | Purified water | 23.3 |
| | Total | 100.0 |

*1 KSG-210 by Shin-Etsu Chemical Co., Ltd.
*2 KSG-15 by Shin-Etsu Chemical Co., Ltd.
*3 KF-6028P by Shin-Etsu Chemical Co., Ltd.
*4 treated with KF-9909 by Shin-Etsu Chemical Co., Ltd.
*5 KP-575 by Shin-Etsu Chemical Co., Ltd.

Preparation of Cosmetic Composition

A W/O liquid foundation was prepared by step A of mixing part of ingredient 4 with ingredient 9 and dispersing ingredient 8 therein uniformly, step B of mixing ingredients 1 to 3, remainder of 4 and ingredients 5 to 7 until uniform, step C of mixing ingredients 10 to 14 and 16 until uniform, and step D of adding C to B while stirring, emulsifying, adding A and ingredient 15 to the emulsion.

The W/O liquid foundation thus obtained was non-sticky, non-oily, light spreading, long lasting, and free of secondary transfer.

Example 41

| W/O cream | | |
|---|---|---|
| | Formulation | Amount (%) |
| 1. | Crosslinked alkyl polyether-modified silicone *1 | 3.0 |
| 2. | Crosslinked alkyl-modified dimethylpolysiloxane *2 | 4.0 |
| 3. | Alkyl-modified branched polyether-modified silicone *3 | 1.0 |
| 4. | Meadowfoam seed oil | 3.5 |
| 5. | Jojoba oil | 2.5 |
| 6. | Macadamia nut oil | 5.0 |
| 7. | Silicone resin solution of Example 3 | 7.5 |
| 8. | Hybrid silicone composite powder *4 | 3.0 |
| 9. | 1,3-Butylene glycol | 8.0 |
| 10. | Glycine | 3.0 |
| 11. | Sodium citrate | 0.2 |
| 12. | Sodium chloride | 0.5 |
| 13. | Preservative | 0.5 |
| 14. | Perfume | 0.2 |
| 15. | Purified water | 58.1 |
| | Total | 100.0 |

*1 KSG-340 by Shin-Etsu Chemical Co., Ltd.
*2 KSG-44 by Shin-Etsu Chemical Co., Ltd.
*3 KF-6038 by Shin-Etsu Chemical Co., Ltd.
*4 KSP-100 by Shin-Etsu Chemical Co., Ltd.

Preparation of Cosmetic Composition

A W/O cream was prepared by step A of mixing ingredients 1 to 8 until uniform, step B of mixing ingredients 9 to 13, and 15 until uniform, step C of slowly adding B to A while stirring, emulsifying, adding ingredient 14 to the emulsion.

The W/O cream thus obtained was non-sticky and non-oily, and sustained a skin moist feeling.

Example 42

| | Cuticle coating agent | |
|---|---|---|
| | Formulation | Amount (%) |
| 1. | Polyether-modified silicone *1 | 3.0 |
| 2. | Polyether-modified silicone *2 | 2.0 |
| 3. | PEG-40 hydrogenated castor oil | 1.0 |
| 4. | Silicone resin solution of Example 4 | 3.0 |
| 5. | Silicone gum liquid *3 | 40.0 |
| 6. | Decamethylcyclopentasiloxane | 40.0 |
| 7. | Alcohol | 4.3 |
| 8. | Preservative | 0.5 |
| 9. | Perfume | 0.2 |
| 10. | Purified water | 6.0 |
| | Total | 100.0 |

*1 KF-6011 by Shin-Etsu Chemical Co., Ltd.
*2 KF-6013 by Shin-Etsu Chemical Co., Ltd.
*3 KF-9028 by Shin-Etsu Chemical Co., Ltd.

Preparation of Cosmetic Composition

A cuticle coating agent was prepared by step A of mixing ingredients 1 to 3 and 7 to 10 until uniform, step B of mixing ingredients 4 to 6 until uniform, step C of adding B to A while stirring, and emulsifying.

The cuticle coating agent thus obtained was light spreading, and effective for preventing the hair from drying up crispy and giving luster and smoothness to the hair.

Example 43

| | Hair treatment | |
|---|---|---|
| | Formulation | Amount (%) |
| 1. | Silicone gum fluid *1 | 5.0 |
| 2. | Diphenyldimethicone *2 | 4.0 |
| 3. | Silicone resin solution of Example 4 | 1.0 |
| 4. | Cetyl octanoate | 1.0 |
| 5. | Cetyl alcohol | 0.5 |
| 6. | Polyether-modified silicone *3 | 1.0 |
| 7. | PEG-60 hydrogenated castor oil | 1.0 |
| 8. | Glyceryl monostearate | 0.5 |
| 9. | Carboxyvinyl polymer (1% aqueous solution) | 25.0 |
| 10. | Xanthan gum (1% aqueous solution) | 7.0 |
| 11. | 1,3-Butylene glycol | 5.0 |
| 12. | Alcohol | 7.0 |
| 13. | Preservative | 0.5 |
| 14. | Perfume | 0.2 |
| 15. | Purified water | 41.3 |
| | Total | 100.0 |

*1 MK-15H by Shin-Etsu Chemical Co., Ltd.
*2 KF-54 by Shin-Etsu Chemical Co., Ltd.
*3 KF-6013 by Shin-Etsu Chemical Co., Ltd.

Preparation of Cosmetic Composition

A hair treatment was prepared by step A of dissolving ingredients 1 to 8 while heating, step B of dissolving ingredients 11 to 15 while heating, step C of adding B to A while stirring, emulsifying, and adding ingredients 8 and 9 to the emulsion.

The hair treatment thus obtained was light spreading and gave luster and smoothness to the hair.

Example 44

| | Nail enamel | |
|---|---|---|
| | Formulation | Amount (%) |
| 1. | Silicone resin solution of Example 2 | 35.0 |
| 2. | Tristrimethylsiloxymethylsilane *1 | 5.0 |
| 3. | Nitrocellulose | 3.0 |
| 4. | Camphor | 0.5 |
| 5. | Acetyltributyl citrate | 1.0 |
| 6. | Dimethyldistearylammonium hectorite | 0.5 |
| 7. | Butyl acetate | 30.0 |
| 8. | Ethyl acetate | 13.0 |
| 9. | Isopropyl alcohol | 5.0 |
| 10. | Color pigment | 7.0 |
| | Total | 100.0 |

*1 TMF-1.5 by Shin-Etsu Chemical Co., Ltd.

Preparation of Cosmetic Composition

A nail enamel was prepared by step A of mixing ingredients 7 to 9, adding ingredients 4 to 6 thereto, and mixing the contents until uniform, step B of adding ingredients 1 to 3 to A and mixing the contents, and step C of adding ingredient 10 to B and mixing the contents.

The nail enamel thus obtained was light spreading, gave luster to the nail and was long lasting.

Example 45

| | Nail enamel overcoat | |
|---|---|---|
| | Formulation | Amount (%) |
| 1. | Silicone resin solution of Example 4 | 6.0 |
| 2. | Nitrocellulose | 17.0 |
| 3. | Alkyd resin | 4.0 |
| 4. | Acetyltriethyl citrate | 5.0 |
| 5. | Butyl acetate | 29.0 |
| 6. | Ethyl acetate | 25.0 |
| 7. | Isopropyl alcohol | 3.0 |
| 8. | n-Butyl alcohol | 1.0 |
| 9. | Toluene | 10.0 |
| | Total | 100.0 |

Preparation of Cosmetic Composition

A nail enamel overcoat was prepared by step A of mixing ingredients 5 to 9, adding ingredient 4 thereto, and mixing the contents until uniform, and step B of adding ingredients 1 to 3 to A and mixing the contents.

The nail enamel overcoat thus obtained was light spreading, increased enamel luster, and was long lasting.

The invention claimed is:

1. A method for preparing a silicone resin represented by the compositional formula (1) and has a weight average molecular weight of 1,000 to 8,000, $$[(C_6H_5)_3SiO_{1/2}]_a[R^1{}_3SiO_{1/2}]_b[R^2{}_2SiO_{2/2}]_c[R^3SiO_{3/2}]_d[SiO_{4/2}]_e \quad (1)$$

wherein $R^1$ is a group, exclusive of phenyl, selected from among $C_1$-$C_8$ alkyl groups, $C_6$-$C_{12}$ aryl groups and $C_1$-$C_8$ fluorinated alkyl groups, $R^2$ and $R^3$ are each independently a group selected from among $C_1$-$C_8$ alkyl groups, $C_6$-$C_{12}$ aryl groups and $C_1$-$C_8$ fluorinated alkyl groups, a is a number of 0.01 to 0.2, b is a number of 0.1 to 0.5, c is a number of 0 to 0.2, d is a number of 0.01 to 0.5, e is a number of 0 to 0.6, a+b+c+d+e is equal to 1.0, $R^1$ to $R^3$ and a to e are selected such that at least one phenyl group is included in the molecule, and a film of the silicone resin having a refractive index of at least 1.48;

the method comprising the following steps (i) and (ii):

(i) effecting hydrolytic condensation of at least one organosilicon compound selected from the general formulae (2) and (3) with at least one compound selected from silanes having the general formulae (4), (5) and (6) and partial hydrolytic condensates thereof in a solventless system or a solvent, $$R^1_3SiOSiR^1_3 \quad (2)$$

$$R^1_3SiOH \quad (3)$$

wherein $R^1$ is as defined above, $$(R^4O)_2SiR^2_2 \quad (4)$$

$$(R^4O)_3SiR^3 \quad (5)$$

$$(R^4O)_4Si \quad (6)$$

wherein $R^2$ and $R^3$ are as defined above, $R^4$ is each independently hydrogen or a substituted or unsubstituted monovalent hydrocarbon group; and (ii) adding triphenylsilanol and a solvent to the hydrolytic condensate, and effecting condensation of the hydrolytic condensate with triphenylsilanol in the presence of a basic catalyst.

2. The method of claim 1 wherein the basic catalyst is sodium hydrogencarbonate or sodium acetate.

3. The method of claim 1, wherein the silicone resin has a phenyl content of at least 30% by weight.

4. The method of claim 1, wherein $R^3$ is phenyl.

5. The method of claim 1, wherein c is 0 in formula (1), $R^1$ is methyl, and $R^3$ is phenyl.

6. The method of claim 1, wherein the solvent in the step (i) comprises at least one selected from the group consisting of toluene, xylene, isoparaffin, tetrahydrofuran, methanol, ethanol, isopropyl alcohol, and butanol.

* * * * *